US005273746A

United States Patent [19]
Payne et al.

[11] Patent Number: 5,273,746
[45] Date of Patent: Dec. 28, 1993

[54] BACILLUS THURINGIENSIS ISOLATES ACTIVE AGAINST PHTHIRAPTERA PESTS

[75] Inventors: Jewel M. Payne; Leslie A. Hickle, both of San Diego, Calif.

[73] Assignee: Mycogen Corporation, San Diego, Calif.

[21] Appl. No.: 828,788

[22] Filed: Jan. 29, 1992

[51] Int. Cl.$^5$ .................. A01N 63/04; A01N 37/18; C07H 21/04
[52] U.S. Cl. ................ 424/93 L; 435/252.5; 435/252.31; 536/23.71; 514/2
[58] Field of Search ............... 424/93 L, DIG. 10; 435/252.31, 252.5; 514/2; 536/27

[56] References Cited

U.S. PATENT DOCUMENTS 4,910,016  3/1990  Gaertner et al. ............... 424/93

OTHER PUBLICATIONS

Couch, T. L. (1980) "Mosquito Pathogenicity of *Bacillus thuringiensis* var. *israelensis*," Developments in Industrial Microbiology 22:61-76.

Beegle, C. C., (1978) "Use of Entomogenous Bacteria in Agroecosystems," Developments in Industrial Microbiology 20:97-104.

Ciordia, H. and W. E. Bizzell, ((1961), "A Preliminary Report on the Effects of *Bacillus thuringiensis* var. *thuringiensis* Berliner on the Development of the Free-Living Stages of Some Cattle Nematodes", Jour. of Parasitology 47:41 (abstract).

Ignoffo, C. M. and V. H. Dropkin, (1977), "Deleterious Effects of the Thermostable Toxin of *Bacillus thuringiensis* on Species of Soil-Inhabiting, Myceliophagus, and Plant-Parasitic Nematodes", Journal of Kansas Entomological Society, 50:(3):394-398.

Bottjer, Kurt P., Leon B. Bone and Sarjeet S. Gill, (1985), "Nematoda: Susceptibility of the Egg to *Bacillus thuringiensis* Toxins", Journal of Parasitology, 60:239-244.

Mulla, Mir S., Brian A. Federici, and Husam A. Darwazeh, "Larvicidal Efficacy of *Bacillus thuringiensis* Serotype H-14 Against Stagnant-Water Mosquitoes and its Effects on Nontarget Organisms", Environmental Entomology 11:788-795, (1982).

Padua, Leodegario E., Michio Ohba and Keio Aizawa, (1984), "Isolation of a *Bacillus thuringiensis* Strain (Serotype 8a:8b) Highly and Selectively Toxin Against Mosquito Larvae", J. of Inv. Pathol. 44:12-17.

Goldberg, Leonard J., and Joel Margalit (1977), "A bacterial Spore Demonstrating Rapid Larvicidal Activity Against *Anopheles sergentii, uranotaenia unguiculata Culex univitattus, Aedes aegypti and Culex pipiens*", Mosquito News 3:355-358.

Lecadet et al. Jour. of Invert. Patho. vol. 49 pp. 37-48 issued 1987.

*Primary Examiner*—Robert A. Wax
*Assistant Examiner*—David Schmickel
*Attorney, Agent, or Firm*—Saliwanchik & Saliwanchik

[57] ABSTRACT

Methods and compositions for the control of lice are described. Specifically, *Bacillus thuringiensis* (B.t.) isolates having anti-lice activity are disclosed. Also described are recombinant hosts which express B.t. genes coding for pesticidal toxins. The B.t. isolates and recombinant proteins are shown to be useful in a method for controlling lice including the sheep louse.

14 Claims, 2 Drawing Sheets

Figure 1

A. *Bacillus thuringiensis* PS36A
B. *Bacillus thuringiensis* PS81F
C. *Bacillus thuringiensis* PS81I
D. *Bacillus thuringiensis* PS81GG
E. *Bacillus thuringiensis* PS91C2
F. *Bacillus thuringiensis* PS192M4

Figure 2

| kDa |
|---|
| 205 |
| 116 |
| 97 |
| 66 |
| 45 |
| 29 |

A B C D E F G H I

A. *Bacillus thuringiensis* PS40D1
B. *Bacillus thuringiensis* PS71M3
C. *Bacillus thuringiensis* PS84C3
D. *Bacillus thuringiensis* PS86A1
E. *Bacillus thuringiensis* PS92J
F. *Bacillus thuringiensis* PS192N1
G. *Bacillus thuringiensis* PS201T6
H. *Bacillus thuringiensis* PS204G6
I. *Bacillus thuringiensis* PS211B2

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 1425 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: BACILLUS THURINGIENSIS
        ( C ) INDIVIDUAL ISOLATE: PS86A1

( v i i ) IMMEDIATE SOURCE:
        ( A ) LIBRARY: LAMBDAGEM (TM) - 11 LIBRARY OF KENNETH NARVA
        ( B ) CLONE: PS86A1-A ( i x ) FEATURE:
        ( A ) NAME/KEY: matpeptide
        ( B ) LOCATION: 1..1425

( x i ) SEQUENCE DESCRIPTION: SEQ ID NO:1:

```
ATGATTATTG  ATAGTAAAAC  GACTTTACCT  AGACATTCAC  TTATTCATAC  AATTAAATTA      60
AATTCTAATA  AGAAATATGG  TCCTGGTGAT  ATGACTAATG  GAAATCAATT  TATTATTTCA     120
AAACAAGAAT  GGGCTACGAT  TGGAGCATAT  ATTCAGACTG  GATTAGGTTT  ACCAGTAAAT     180
GAACAACAAT  TAAGAACACA  TGTTAATTTA  AGTCAGGATA  TATCAATACC  TAGTGATTTT     240
TCTCAATTAT  ATGATGTTTA  TTGTTCTGAT  AAAACTTCAG  CAGAATGGTG  GAATAAAAAT     300
TTATATCCTT  TAATTATTAA  ATCTGCTAAT  GATATTGCTT  CATATGGTTT  TAAAGTTGCT     360
GGTGATCCTT  CTATTAAGAA  AGATGGATAT  TTTAAAAAAT  TGCAAGATGA  ATTAGATAAT     420
ATTGTTGATA  ATAATTCCGA  TGATGATGCA  ATAGCTAAAG  CTATTAAAGA  TTTTAAAGCG     480
CGATGTGGTA  TTTTAATTAA  AGAAGCTAAA  CAATATGAAG  AAGCTGCAAA  AAATATTGTA     540
ACATCTTTAG  ATCAATTTTT  ACATGGTGAT  CAGAAAAAAT  TAGAAGGTGT  TATCAATATT     600
CAAAAACGTT  TAAAAGAAGT  TCAAACAGCT  CTTAATCAAG  CCCATGGGGA  AAGTAGTCCA     660
GCTCATAAAG  AGTTATTAGA  AAAAGTAAAA  AATTTAAAAA  CAACATTAGA  AAGGACTATT     720
AAAGCTGAAC  AAGATTTAGA  GAAAAAAGTA  GAATATAGTT  TTCTATTAGG  ACCATTGTTA     780
GGATTTGTTG  TTTATGAAAT  TCTTGAAAAT  ACTGCTGTTC  AGCATATAAA  AAATCAAATT     840
GATGAGATAA  AGAAACAATT  AGATTCTGCT  CAGCATGATT  TGGATAGAGA  TGTTAAAATT     900
```

| ATAGGAATGT | TAAATAGTAT | TAATACAGAT | ATTGATAATT | TATATAGTCA | AGGACAAGAA | 960 |
| GCAATTAAAG | TTTTCCAAAA | GTTACAAGGT | ATTTGGGCTA | CTATTGGAGC | TCAAATAGAA | 1020 |
| AATCTTAGAA | CAACGTCGTT | ACAAGAAGTT | CAAGATTCTG | ATGATGCTGA | TGAGATACAA | 1080 |
| ATTGAACTTG | AGGACGCTTC | TGATGCTTGG | TTAGTTGTGG | CTCAAGAAGC | TCGTGATTTT | 1140 |
| ACACTAAATG | CTTATTCAAC | TAATAGTAGA | CAAAATTTAC | CGATTAATGT | TATATCAGAT | 1200 |
| TCATGTAATT | GTTCAACAAC | AAATATGACA | TCAAATCAAT | ACAGTAATCC | AACAACAAAT | 1260 |
| ATGACATCAA | ATCAATATAT | GATTTCACAT | GAATATACAA | GTTTACCAAA | TAATTTTATG | 1320 |
| TTATCAAGAA | ATAGTAATTT | AGAATATAAA | TGTCCTGAAA | ATAATTTTAT | GATATATTGG | 1380 |
| TATAATAATT | CGGATTGGTA | TAATAATTCG | GATTGGTATA | ATAAT | | 1425 |

(2) INFORMATION FOR SEQ ID NO:2:

(i) SEQUENCE CHARACTERISTICS:
      (A) LENGTH: 475 amino acids
      (B) TYPE: amino acid
      (C) STRANDEDNESS: single
      (D) TOPOLOGY: linear (ii) MOLECULE TYPE: protein (iii) HYPOTHETICAL: YES (iv) ANTI-SENSE: NO (vi) ORIGINAL SOURCE:
      (A) ORGANISM: BACILLUS THURINGIENSIS
      (C) INDIVIDUAL ISOLATE: PS86A1

(ix) FEATURE:
      (A) NAME/KEY: Protein
      (B) LOCATION: 1..475

(xi) SEQUENCE DES

```
Thr Ala Leu Asn Gln Ala His Gly Glu Ser Ser Pro Ala His Lys Glu
    210             215                 220

Leu Leu Glu Lys Val Lys Asn Leu Lys Thr Thr Leu Glu Arg Thr Ile
225             230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305             310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
    355                 360                 365

Ala Trp Leu Val Val Ala Gln Glu Ala Arg Asp Phe Thr Leu Asn Ala
370                 375                 380

Tyr Ser Thr Asn Ser Arg Gln Asn Leu Pro Ile Asn Val Ile Ser Asp
385             390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Gln Tyr Met Ile Ser His Glu Tyr
            420                 425                 430

Thr Ser Leu Pro Asn Asn Phe Met Leu Ser Arg Asn Ser Asn Leu Glu
        435                 440                 445

Tyr Lys Cys Pro Glu Asn Asn Phe Met Ile Tyr Trp Tyr Asn Asn Ser
    450                 455                 460

Asp Trp Tyr Asn Asn Ser Asp Trp Tyr Asn Asn
465             470                 475
```

( 2 ) INFORMATION FOR SEQ ID NO:3:

( i ) SEQUENCE CHARACTERISTICS:
        ( A ) LENGTH: 1931 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: BACILLUS THURINGIENSIS
        ( B ) STRAIN: NIGERIENSIS
        ( C ) INDIVIDUAL ISOLATE: PS40D1

( v i i ) IMMEDIATE SOURCE:
        ( A ) LIBRARY: LAMBDAGEM (TM) - 11 LIBRARY OF FRANK GAERTNER
        ( B ) CLONE: 40D1

( x i ) SEQUENCE DESCRIPTION: SEQ ID NO:3:

```
ATGAATCCGA ACAATCGAAG TGAACATGAT ACAATAAAAA CTACTGAAAA TAATGAGGTG     60
CCAACTAACC ATGTTCAATA TCCTTTAGCG GAAACTCCAA ATCCAACACT AGAAGATTTA    120
AATTATAAAG AGTTTTTAAG AATGACTGCA GATAATAATA CGGAAGCACT AGATAGCTCT    180
```

-continued

```
ACAACAAAAG ATGTCATTCA AAAAGGCATT TCCGTAGTAG GTGATCTCCT AGGCGTAGTA  240
GGTTTCCCGT TTGGTGGAGC GCTTGTTTCG TTTTATACAA ACTTTTTAAA TACTATTTGG  300
CCAAGTGAAG ACCCGTGGAA GGCTTTTATG GAACAAGTAG AAGCATTGAT GGATCAGAAA  360
ATAGCTGATT ATGCAAAAAA TAAAGCTCTT GCAGAGTTAC AGGGCCTTCA AAATAATGTC  420
GAAGATTATG TGAGTGCATT GAGTTCATGG CAAAAAAATC CTGTGAGTTC ACGAAATCCA  480
CATAGCCAGG GGCGGATAAG AGAGCTGTTT TCTCAAGCAG AAAGTCATTT TCGTAATTCA  540
ATGCCTTCGT TTGCAATTTC TGGATACGAG GTTCTATTTC TAACAACATA TGCACAAGCT  600
GCCAACACAC ATTTATTTTT ACTAAAAGAC GCTCAAATTT ATGGAGAAGA ATGGGGATAC  660
GAAAAAGAAG ATATTGCTGA ATTTTATAAA AGACAACTAA AACTTACGCA AGAATATACG  720
ACCATTGTGT CAAATGGTAT AATGTTGGAT TAGATAAATT AAGAGGTTCA TCTTATGAAT  780
CTTGGGTAAA CTTTAACCGT TATCGCAGAG AGATGACATT AACAGTATTA GATTTAATTG  840
CACTATTTCC ATTGTATGAT GTTCGGCTAT ACCCAAAAGA AGTTAAAACC GAATTAACAA  900
GAGACGTTTT AACAGATCCA ATTGTCGGAG TCAACAACCT TAGGGGCTAT GGAACAACCT  960
TCTCTAATAT AGAAAATTAT ATTCGAAAAC CACATCTATT TGACTATCTG CATAGAATTC 1020
AATTTCACAC GCGGTTCCAA CCAGGATATT ATGGAAATGA CTCTTTCAAT TATTGGTCCG 1080
GTAATTATGT TTCAACTAGA CCAAGCATAG GATCAAATGA TATAATCACA TCTCCATTCT 1140
ATGGAAATAA ATCCAGTGAA CCTGTACAAA ATTTAGAATT TAATGGAGAA AAAGTCTATA 1200
GAGCCGTAGC AAATACAAAT CTTGCGGTCT GGCCGTCCGC TGTATATTCA GGTGTTACAA 1260
AAGTGGAATT TAGCCAATAT AATGATCAAA CAGATGAAGC AAGTACACAA ACGTACGACT 1320
CAAAAAGAAA TGTTGGCGCG GTCAGCTGGG ATTCTATCGA TCAATTGCCT CCAGAAACAA 1380
CAGATGAACC TCTAGAAAAG GGATATAGCC ATCAACTCAA TTATGTAATG TGCTTTTTAA 1440
TGCAGGGTAG TAGAGGAACA ATCCCAGTGT TAACTTGGAC ACATAAAAGT GTAGACTTTT 1500
TTAACATGAT TGATTCGAAA AAAATTACAC AACTTCCGTT AGTAAAGGCA TATAAGTTAC 1560
AATCTGGTGC TTCCGTTGTC GCAGGTCCTA GGTTTACAGG AGGAGATATC ATTCAATGCA 1620
CAGAAAATGG AAGTGCGGCA ACTATTTACG TTACACCGGA TGTGTCGTAC TCTCAAAAAT 1680
ATCGAGCTAG AATTCATTAT GCTTCTACAT CTCAGATAAC ATTTACACTC AGTTTAGACG 1740
GGGCACCATT TAATCAATAC TATTTCGATA AAACGATAAA TAAAGGAGAC ACATTAACGT 1800
ATAATTCATT TAATTTAGCA AGTTTCAGCA CACCATTCGA ATTATCAGGG AATAACTTAC 1860
AAATAGGCGT CACAGGATTA AGTGCTGGAG ATAAAGTTTA TATAGACAAA ATTGAATTTA 1920
TTCCAGTGAA T                                                     1931
```

( 2 ) INFORMATION FOR SEQ ID NO:4:

( i ) SEQUENCE CHARACTERISTICS:
( A ) LENGTH: 644 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: BACILLUS THURINGIENSIS
( B ) STRAIN: NIGERIENSIS
( C ) INDIVIDUAL ISOLATE: PS40D1

( v i i ) IMMEDIATE SOURCE:

(A) LIBRARY: LAMBDAGEM (TM) - 11 LIBRARY OF FRANK GAERTNER
(B) CLONE: 40D1

(xi) SEQUENCE DESCRIPTION: SEQ ID NO:4:

| Met | Asn | Pro | Asn | Asn | Arg | Ser | Glu | His | Asp | Thr | Ile | Lys | Thr | Thr | Glu |
|---|---|---|---|---|---|---|---|---|---|---|---|---|---|---|---|
| 1 | | | | 5 | | | | | 10 | | | | | 15 | |

| Asn | Asn | Glu | Val | Pro | Thr | Asn | His | Val | Gln | Tyr | Pro | Leu | Ala | Glu | Thr |
|---|---|---|---|---|---|---|---|---|---|---|---|---|---|---|---|
| | | | 20 | | | | | 25 | | | | | 30 | | |

| Pro | Asn | Pro | Thr | Leu | Glu | Asp | Leu | Asn | Tyr | Lys | Glu | Phe | Leu | Arg | Met |
|---|---|---|---|---|---|---|---|---|---|---|---|---|---|---|---|
| | | 35 | | | | 40 | | | | | 45 | | | | |

| Thr | Ala | Asp | Asn | Asn | Thr | Glu | Ala | Leu | Asp | Ser | Ser | Thr | Thr | Lys | Asp |
|---|---|---|---|---|---|---|---|---|---|---|---|---|---|---|---|
| | 50 | | | | | 55 | | | | | 60 | | | | |

| Val | Ile | Gln | Lys | Gly | Ile | Ser | Val | Val | Gly | Asp | Leu | Leu | Gly | Val | Val |
|---|---|---|---|---|---|---|---|---|---|---|---|---|---|---|---|
| 65 | | | | | 70 | | | | | 75 | | | | | 80 |

| Gly | Phe | Pro | Phe | Gly | Gly | Ala | Leu | Val | Ser | Phe | Tyr | Thr | Asn | Phe | Leu |
|---|---|---|---|---|---|---|---|---|---|---|---|---|---|---|---|
| | | | | 85 | | | | | 90 | | | | | 95 | |

| Asn | Thr | Ile | Trp | Pro | Ser | Glu | Asp | Pro | Trp | Lys | Ala | Phe | Met | Glu | Gln |
|---|---|---|---|---|---|---|---|---|---|---|---|---|---|---|---|
| | | | 100 | | | | | 105 | | | | | 110 | | |

| Val | Glu | Ala | Leu | Met | Asp | Gln | Lys | Ile | Ala | Asp | Tyr | Ala | Lys | Asn | Lys |
|---|---|---|---|---|---|---|---|---|---|---|---|---|---|---|---|
| | | | 115 | | | | 120 | | | | | 125 | | | |

| Ala | Leu | Ala | Glu | Leu | Gln | Gly | Leu | Gln | Asn | Asn | Val | Glu | Asp | Tyr | Val |
|---|---|---|---|---|---|---|---|---|---|---|---|---|---|---|---|
| | 130 | | | | | 135 | | | | | 140 | | | | |

| Ser | Ala | Leu | Ser | Ser | Trp | Gln | Lys | Asn | Pro | Val | Ser | Ser | Arg | Asn | Pro |
|---|---|---|---|---|---|---|---|---|---|---|---|---|---|---|---|
| 145 | | | | | 150 | | | | | 155 | | | | | 160 |

| His | Ser | Gln | Gly | Arg | Ile | Arg | Glu | Leu | Phe | Ser | Gln | Ala | Glu | Ser | His |
|---|---|---|---|---|---|---|---|---|---|---|---|---|---|---|---|
| | | | | 165 | | | | | 170 | | | | | 175 | |

| Phe | Arg | Asn | Ser | Met | Pro | Ser | Phe | Ala | Ile | Ser | Gly | Tyr | Glu | Val | Leu |
|---|---|---|---|---|---|---|---|---|---|---|---|---|---|---|---|
| | | | 180 | | | | | 185 | | | | | 190 | | |

| Phe | Leu | Thr | Thr | Tyr | Ala | Gln | Ala | Ala | Asn | Thr | His | Leu | Phe | Leu | Leu |
|---|---|---|---|---|---|---|---|---|---|---|---|---|---|---|---|
| | | 195 | | | | | 200 | | | | | 205 | | | |

| Lys | Asp | Ala | Gln | Ile | Tyr | Gly | Glu | Glu | Trp | Gly | Tyr | Glu | Lys | Glu | Asp |
|---|---|---|---|---|---|---|---|---|---|---|---|---|---|---|---|
| | 210 | | | | | 215 | | | | | 220 | | | | |

| Ile | Ala | Glu | Phe | Tyr | Lys | Arg | Gln | Leu | Lys | Leu | Thr | Gln | Glu | Tyr | Thr |
|---|---|---|---|---|---|---|---|---|---|---|---|---|---|---|---|
| 225 | | | | | 230 | | | | | 235 | | | | | 240 |

| Asp | His | Cys | Val | Lys | Trp | Tyr | Asn | Val | Gly | Leu | Asp | Lys | Leu | Arg | Gly |
|---|---|---|---|---|---|---|---|---|---|---|---|---|---|---|---|
| | | | | 245 | | | | | 250 | | | | | 255 | |

| Ser | Ser | Tyr | Glu | Ser | Trp | Val | Asn | Phe | Asn | Arg | Tyr | Arg | Arg | Glu | Met |
|---|---|---|---|---|---|---|---|---|---|---|---|---|---|---|---|
| | | | 260 | | | | | 265 | | | | | 270 | | |

| Thr | Leu | Thr | Val | Leu | Asp | Leu | Ile | Ala | Leu | Phe | Pro | Leu | Tyr | Asp | Val |
|---|---|---|---|---|---|---|---|---|---|---|---|---|---|---|---|
| | | 275 | | | | | 280 | | | | | 285 | | | |

| Arg | Leu | Tyr | Pro | Lys | Glu | Val | Lys | Thr | Glu | Leu | Thr | Arg | Asp | Val | Leu |
|---|---|---|---|---|---|---|---|---|---|---|---|---|---|---|---|
| | 290 | | | | | 295 | | | | | 300 | | | | |

| Thr | Asp | Pro | Ile | Val | Gly | Val | Asn | Asn | Leu | Arg | Gly | Tyr | Gly | Thr | Thr |
|---|---|---|---|---|---|---|---|---|---|---|---|---|---|---|---|
| 305 | | | | | 310 | | | | | 315 | | | | | 320 |

| Phe | Ser | Asn | Ile | Glu | Asn | Tyr | Ile | Arg | Lys | Pro | His | Leu | Phe | Asp | Tyr |
|---|---|---|---|---|---|---|---|---|---|---|---|---|---|---|---|
| | | | | 325 | | | | | 330 | | | | | 335 | |

| Leu | His | Arg | Ile | Gln | Phe | His | Thr | Arg | Phe | Gln | Pro | Gly | Tyr | Tyr | Gly |
|---|---|---|---|---|---|---|---|---|---|---|---|---|---|---|---|
| | | | 340 | | | | | 345 | | | | | 350 | | |

| Asn | Asp | Ser | Phe | Asn | Tyr | Trp | Ser | Gly | Asn | Tyr | Val | Ser | Thr | Arg | Pro |
|---|---|---|---|---|---|---|---|---|---|---|---|---|---|---|---|
| | | 355 | | | | | 360 | | | | | 365 | | | |

| Ser | Ile | Gly | Ser | Asn | Asp | Ile | Ile | Thr | Ser | Pro | Phe | Tyr | Gly | Asn | Lys |
|---|---|---|---|---|---|---|---|---|---|---|---|---|---|---|---|
| | 370 | | | | | 375 | | | | | 380 | | | | |

| Ser | Ser | Glu | Pro | Val | Gln | Asn | Leu | Glu | Phe | Asn | Gly | Glu | Lys | Val | Tyr |
|---|---|---|---|---|---|---|---|---|---|---|---|---|---|---|---|
| 385 | | | | | 390 | | | | | 395 | | | | | 400 |

| Arg | Ala | Val | Ala | Asn | Thr | Asn | Leu | Ala | Val | Trp | Pro | Ser | Ala | Val | Tyr |
|---|---|---|---|---|---|---|---|---|---|---|---|---|---|---|---|
| | | | | 405 | | | | | 410 | | | | | 415 | |

-continued

Ser Gly Val Thr Lys Val Glu Phe Ser Gln Tyr Asn Asp Gln Thr Asp
420 425 430

Glu Ala Ser Thr Gln Thr Tyr Asp Ser Lys Arg Asn Val Gly Ala Val
435 440 445

Ser Trp Asp Ser Ile Asp Gln Leu Pro Pro Glu Thr Thr Asp Glu Pro
450 455 460

Leu Glu Lys Gly Tyr Ser His Gln Leu Asn Tyr Val Met Cys Phe Leu
465 470 475 480

Met Gln Gly Ser Arg Gly Thr Ile Pro Val Leu Thr Trp Thr His Lys
485 490 495

Ser Val Asp Phe Phe Asn Met Ile Asp Ser Lys Lys Ile Thr Gln Leu
500 505 510

Pro Leu Val Lys Ala Tyr Lys Leu Gln Ser Gly Ala Ser Val Val Ala
515 520 525

Gly Pro Arg Phe Thr Gly Gly Asp Ile Ile Gln Cys Thr Glu Asn Gly
530 535 540

Ser Ala Ala Thr Ile Tyr Val Thr Pro Asp Val Ser Tyr Ser Gln Lys
545 550 555 560

Tyr Arg Ala Arg Ile His Tyr Ala Ser Thr Ser Gln Ile Thr Phe Thr
565 570 575

Leu Ser Leu Asp Gly Ala Pro Phe Asn Gln Tyr Tyr Phe Asp Lys Thr
580 585 590

Ile Asn Lys Gly Asp Thr Leu Thr Tyr Asn Ser Phe Asn Leu Ala Ser
595 600 605

Phe Ser Thr Pro Phe Glu Leu Ser Gly Asn Asn Leu Gln Ile Gly Val
610 615 620

Thr Gly Leu Ser Ala Gly Asp Lys Val Tyr Ile Asp Lys Ile Glu Phe
625 630 635 640

Ile Pro Val Asn ( 2 ) INFORMATION FOR SEQ ID NO:5:

( i ) SEQUENCE CHARACTERISTICS:
( A ) LENGTH: 3513 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: BACILLUS THURINGIENSIS
( B ) STRAIN: KENYAE
( C ) INDIVIDUAL ISOLATE: PS81F ( v i i ) IMMEDIATE SOURCE:
( A ) LIBRARY: LAMBDAGEM (TM) - 11 LIBRARY OF AUGUST SICK
( B ) CLONE: 81F ( x i ) SEQUENCE DESCRIPTION: SEQ ID NO:5:

ATGGAGATAG TGAATAATCA GAATCAATGC GTGCCTTATA ATTGTTTAAA TAATCCTGAA 60

AATGAGATAT TAGATATTGA AAGGTCAAAT AGTACTGTAG CAACAAACAT CGCCTTGGAG 120

ATTAGTCGTC TGCTCGCTTC CGCAACTCCA ATAGGGGGGA TTTTATTAGG ATTGTTTGAT 180

GCAATATGGG GGTCTATAGG CCCTTCACAA TGGGATTTAT TTTTAGAGCA AATTGAGCTA 240

TTGATTGACC AAAAAATAGA GGAATTCGCT AGAAACCAGG CAATTTCTAG ATTAGAAGGG 300

ATAAGCAGTC TGTACGGAAT TTATACAGAA GCTTTTAGAG AGTGGGAAGC AGATCCTACT 360

```
AATCCAGCAT TAAAAGAAGA GATGCGTACT CAATTTAATG ACATGAACAG TATTCTTGTA      420
ACAGCTATTC CTCTTTTTTC AGTTCAAAAT TATCAAGTCC CATTTTTATC AGTATATGTT      480
CAAGCTGCAA ATTTACATTT ATCGGTTTTG AGAGATGTTT CAGTGTTTGG GCAGGCTTGG      540
GGATTTGATA TAGCAACAAT AAATAGTCGT TATAATGATC TGACTAGACT TATTCCTATA      600
TATACAGATT ATGCTGTACG CTGGTACAAT ACGGGATTAG ATCGCTTACC ACGAACTGGT      660
GGGCTGCGAA ACTGGGCAAG ATTTAATCAG TTTAGAAGAG AGTTAACAAT ATCAGTATTA      720
GATATTATTT CTTTTTTCAG AAATTACGAT TCTAGATTAT ATCCAATTCC AACAAGCTCC      780
CAATTAACGC GGGAAGTATA TACAGATCCG GTAATTAATA TAACTGACTA TAGAGTTGGC      840
CCCAGCTTCG AGAATATTGA GAACTCAGCC ATTAGAAGCC CCCACCTTAT GGACTTCTTA      900
AATAATTTGA CCATTGATAC GGATTTGATT AGAGGTGTTC ACTATTGGGC AGGGCATCGT      960
GTAACTTCTC ATTTTACAGG TAGTTCTCAA GTGATAACAA CCCCTCAATA TGGGATAACC     1020
GCAAATGCGG AACCAAGACG AACTATTGCT CCTAGTACTT TTCCAGGTCT TAACCTATTT     1080
TATAGAACAT TATCAAATCC TTTCTTCCGA AGATCAGAAA ATATTACTCC TACCTTAGGG     1140
ATAAATGTAG TACAGGGAGT AGGGTTCATT CAACCAAATA ATGCTGAAGT TCTATATAGA     1200
AGTAGGGGGA CAGTAGATTC TCTTAATGAG TTACCAATTG ATGGTGAGAA TTCATTAGTT     1260
GGATATAGTC ATCGATTAAG TCATGTTACA CTAACCAGGT CGTTATATAA TACTAATATA     1320
ACTAGCCTGC CAACATTTGT TTGGACACAT CACAGTGCTA CTAATACAAA TACAATTAAT     1380
CCAGATATTA TTACACAAAT ACCTTTAGTG AAAGGATTTA GACTTGGTGG TGGCACCTCT     1440
GTCATTAAAG GACCAGGATT TACAGGAGGG GATATCCTTC GAAGAAATAC CATTGGTGAG     1500
TTTGTGTCTT TACAAGTCAA TATTAACTCA CCAATTACCC AAAGATACCG TTTAAGATTT     1560
CGTTATGCTT CCAGTAGGGA TGCACGAATT ACTGTAGCGA TAGGAGGACA AATTAGAGTA     1620
GATATGACCC TTGAAAAAAC CATGGAAATT GGGGAGAGCT TAACATCTAG AACATTTAGC     1680
TATACCAATT TTAGTAATCC TTTTTCATTT AGGGCTAATC CAGATATAAT TAGAATAGCT     1740
GAAGAACTTC CTATTCGTGG TGGTGAGCTT TATATAGATA AAATTGAACT TATTCTAGCA     1800
GATGCAACAT TTGAAGAAGA ATATGATTTG GAAAGAGCAC AGAAGGCGGT GAATGCCCTG     1860
TTTACTTCTA CAAATCAACT AGGGCTAAAA ACAGATGTGA CGGATTATCA TATTGATCAA     1920
GTTTCCAATT TAGTTGAGTG TTTATCGGAT GAATTTTGTC TGGATGAAAA GAGAGAATTA     1980
TCCGAGAAAG TCAAACATGC GAAGCGACTC AGTGATGAAC GGAATTTACT TCAAGATCCA     2040
AACTTCAGAG GGATCAATAG GCAACCAGAC CGTGGCTGGA GAGGAAGCAC GGATATTACT     2100
ATCCAAGGTG GAGATGACGT ATTCAAAGAG AATTACGTCA CATTACCGGG TACCTTTGAT     2160
GAGTGCTATC CAACGTATTT ATATCAAAAA ATAGATGAGT CGAAGTTAAA AGCTTATACC     2220
CGCTATGAAT TAAGAGGGTA TATCGAGGAT AGTCAAGACT TAGAAATCTA TTTAATTCGC     2280
TACAATGCAA AACACGAGAC AGTAAACGTG CCAGGTACGG GTTCCTTATG GCCGCTTTCA     2340
GCCCAAAGTC CAATCGGAAA GTGTGGAGAA CCGAATCGAT GCGCGCCACA CCTTGAATGG     2400
AATCCTAATC TAGATTGCTC CTGCAGAGAC GGGGAAAAAT GTGCCCATCA TTCCCATCAT     2460
TTCTCCTTGG ACATTGATGT TGGATGTACA GACTTAAATG AGGACTTAGG TGTATGGGTG     2520
ATATTCAAGA TTAAGACACA AGATGGCTAT GCAAGACTAG GAAATCTAGA GTTTCTCGAA     2580
GAGAAACCAC TATTAGGGGA AGCACTAGCT CGTGTGAAAA GAGCGGAGAA AAAATGGAGA     2640
GACAAATGCG AAAAATTGGA ATGGGAAACA AATATTGTTT ATAAAGAGGC AAAAGAATCT     2700
GTAGATGCTT TATTTGTAAA CTCTCAATAT GATAGATTAC AAGCGGATAC GAATATCGCG     2760
ATGATTCATG CGGCAGATAA ACGCGTTCAT AGCATTCGAG AAGCGTATCT GCCAGAGCTG     2820
```

```
TCTGTGATTC CGGGTGTCAA TGCGGCTATT TTTGAAGAAT TAGAAGGGCG TATTTTCACT    2880

GCATTCTCCC TATATGATGC GAGAAATGTC ATTAAAAATG GCGATTTCAA TAATGGCTTA    2940

TCATGCTGGA ACGTGAAAGG GCATGTAGAT GTAGAAGAAC AGAACAACCA TCGTTCGGTC    3000

CTTGTTGTTC CAGAATGGGA AGCAGAAGTG TCACAAGAAG TTCGTGTTTG TCCGGGTCGT    3060

GGCTATATCC TTCGTGTTAC AGCGTACAAA GAGGGATATG GAGAGGGCTG TGTAACGATT    3120

CATGAGATCG AAGACAATAC AGACGAACTG AAATTCAGCA ACTGTGTAGA AGAGGAAGTA    3180

TATCCAAACA ACACGGTAAC GTGTAATAAT TATACTGCGA CTCAAGAAGA ACATGAGGGT    3240

ACGTACACTT CCCGTAATCG AGGATATGAC GAAGCCTATG AAAGCAATTC TTCTGTACAT    3300

GCGTCAGTCT ATGAAGAAAA ATCGTATACA GATAGACGAA GAGAGAATCC TTGTGAATCT    3360

AACAGAGGAT ATGGGGATTA CACACCACTA CCAGCTGGCT ATGTGACAAA AGAATTAGAG    3420

TACTTCCCAG AAACCGATAA GGTATGGATT GAGATCGGAG AAACGGAAGG AACATTCATC    3480

GTGGACAGCG TGGAATTACT TCTTATGGAG GAA                                3513
```

( 2 ) INFORMATION FOR SEQ ID NO:6:

( i ) SEQUENCE CHARACTERISTICS:
        ( A ) LENGTH: 1171 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
        ( A ) ORGANISM: BACILLUS THURINGIENSIS
        ( B ) STRAIN: KENYAE
        ( C ) INDIVIDUAL ISOLATE: PS81F ( v i i ) IMMEDIATE SOURCE:
        ( A ) LIBRARY: LAMBDAGEM (TM) - 11 LIBRARY OF AUGUST SICK
        ( B ) CLONE: 81F ( x i ) SEQUENCE DESCRIPTION: SEQ ID NO:6:

```
Met Glu Ile Val Asn Asn Gln Asn Gln Cys Val Pro Tyr Asn Cys Leu
 1               5                  10                  15

Asn Asn Pro Glu Asn Glu Ile Leu Asp Ile Glu Arg Ser Asn Ser Thr
                20                  25                  30

Val Ala Thr Asn Ile Ala Leu Glu Ile Ser Arg Leu Leu Ala Ser Ala
                35                  40                  45

Thr Pro Ile Gly Gly Ile Leu Leu Gly Leu Phe Asp Ala Ile Trp Gly
        50                  55                  60

Ser Ile Gly Pro Ser Gln Trp Asp Leu Phe Leu Glu Gln Ile Glu Leu
65                  70                  75                  80

Leu Ile Asp Gln Lys Ile Glu Glu Phe Ala Arg Asn Gln Ala Ile Ser
                85                  90                  95

Arg Leu Glu Gly Ile Ser Ser Leu Tyr Gly Ile Tyr Thr Glu Ala Phe
                100                 105                 110

Arg Glu Trp Glu Ala Asp Pro Thr Asn Pro Ala Leu Lys Glu Glu Met
            115                 120                 125

Arg Thr Gln Phe Asn Asp Met Asn Ser Ile Leu Val Thr Ala Ile Pro
    130                 135                 140

Leu Phe Ser Val Gln Asn Tyr Gln Val Pro Phe Leu Ser Val Tyr Val
145                 150                 155                 160

Gln Ala Ala Asn Leu His Leu Ser Val Leu Arg Asp Val Ser Val Phe
```

-continued

|     |     |     | 165 |     |     |     |     | 170 |     |     |     |     | 175 |     |
|-----|-----|-----|-----|-----|-----|-----|-----|-----|-----|-----|-----|-----|-----|-----|

Gly Gln Ala Trp Gly Phe Asp Ile Ala Thr Ile Asn Ser Arg Tyr Asn
            180                 185                 190

Asp Leu Thr Arg Leu Ile Pro Ile Tyr Thr Asp Tyr Ala Val Arg Trp
            195                 200                 205

Tyr Asn Thr Gly Leu Asp Arg Leu Pro Arg Thr Gly Gly Leu Arg Asn
210                     215                 220

Trp Ala Arg Phe Asn Gln Phe Arg Arg Glu Leu Thr Ile Ser Val Leu
225                     230                 235                 240

Asp Ile Ile Ser Phe Phe Arg Asn Tyr Asp Ser Arg Leu Tyr Pro Ile
                245                 250                 255

Pro Thr Ser Ser Gln Leu Thr Arg Glu Val Tyr Thr Asp Pro Val Ile
                260                 265                 270

Asn Ile Thr Asp Tyr Arg Val Gly Pro Ser Phe Glu Asn Ile Glu Asn
            275                 280                 285

Ser Ala Ile Arg Ser Pro His Leu Met Asp Phe Leu Asn Asn Leu Thr
            290                 295                 300

Ile Asp Thr Asp Leu Ile Arg Gly Val His Tyr Trp Ala Gly His Arg
305                     310                 315                 320

Val Thr Ser His Phe Thr Gly Ser Ser Gln Val Ile Thr Thr Pro Gln
                325                 330                 335

Tyr Gly Ile Thr Ala Asn Ala Glu Pro Arg Arg Thr Ile Ala Pro Ser
            340                 345                 350

Thr Phe Pro Gly Leu Asn Leu Phe Tyr Arg Thr Leu Ser Asn Pro Phe
            355                 360                 365

Phe Arg Arg Ser Glu Asn Ile Thr Pro Thr Leu Gly Ile Asn Val Val
370                     375                 380

Gln Gly Val Gly Phe Ile Gln Pro Asn Asn Ala Glu Val Leu Tyr Arg
385                     390                 395                 400

Ser Arg Gly Thr Val Asp Ser Leu Asn Glu Leu Pro Ile Asp Gly Glu
                405                 410                 415

Asn Ser Leu Val Gly Tyr Ser His Arg Leu Ser His Val Thr Leu Thr
            420                 425                 430

Arg Ser Leu Tyr Asn Thr Asn Ile Thr Ser Leu Pro Thr Phe Val Trp
            435                 440                 445

Thr His His Ser Ala Thr Asn Thr Asn Thr Ile Asn Pro Asp Ile Ile
450                     455                 460

Thr Gln Ile Pro Leu Val Lys Gly Phe Arg Leu Gly Gly Gly Thr Ser
465                     470                 475                 480

Val Ile Lys Gly Pro Gly Phe Thr Gly Gly Asp Ile Leu Arg Arg Asn
                485                 490                 495

Thr Ile Gly Glu Phe Val Ser Leu Gln Val Asn Ile Asn Ser Pro Ile
            500                 505                 510

Thr Gln Arg Tyr Arg Leu Arg Phe Arg Tyr Ala Ser Ser Arg Asp Ala
            515                 520                 525

Arg Ile Thr Val Ala Ile Gly Gly Gln Ile Arg Val Asp Met Thr Leu
530                     535                 540

Glu Lys Thr Met Glu Ile Gly Glu Ser Leu Thr Ser Arg Thr Phe Ser
545                     550                 555                 560

Tyr Thr Asn Phe Ser Asn Pro Phe Ser Phe Arg Ala Asn Pro Asp Ile
                565                 570                 575

Ile Arg Ile Ala Glu Glu Leu Pro Ile Arg Gly Gly Glu Leu Tyr Ile
            580                 585                 590

Asp Lys Ile Glu Leu Ile Leu Ala Asp Ala Thr Phe Glu Glu Glu Tyr
            595                 600                 605

-continued

| | | | | | | | | | | | | | |
|---|---|---|---|---|---|---|---|---|---|---|---|---|---|
| Asp | Leu | Glu | Arg | Ala | Gln | Lys | Ala | Val | Asn | Ala | Leu | Phe | Thr | Ser | Thr |
| 610 | | | | | 615 | | | | | 620 | | | | |
| Asn | Gln | Leu | Gly | Leu | Lys | Thr | Asp | Val | Thr | Asp | Tyr | His | Ile | Asp | Gln |
| 625 | | | | | 630 | | | | | 635 | | | | | 640 |
| Val | Ser | Asn | Leu | Val | Glu | Cys | Leu | Ser | Asp | Glu | Phe | Cys | Leu | Asp | Glu |
| | | | | 645 | | | | | 650 | | | | | 655 | |
| Lys | Arg | Glu | Leu | Ser | Glu | Lys | Val | Lys | His | Ala | Lys | Arg | Leu | Ser | Asp |
| | | | 660 | | | | | 665 | | | | | 670 | | |
| Glu | Arg | Asn | Leu | Leu | Gln | Asp | Pro | Asn | Phe | Arg | Gly | Ile | Asn | Arg | Gln |
| | | 675 | | | | | 680 | | | | | 685 | | | |
| Pro | Asp | Arg | Gly | Trp | Arg | Gly | Ser | Thr | Asp | Ile | Thr | Ile | Gln | Gly | Gly |
| | 690 | | | | | 695 | | | | | 700 | | | | |
| Asp | Asp | Val | Phe | Lys | Glu | Asn | Tyr | Val | Thr | Leu | Pro | Gly | Thr | Phe | Asp |
| 705 | | | | | 710 | | | | | 715 | | | | | 720 |
| Glu | Cys | Tyr | Pro | Thr | Tyr | Leu | Tyr | Gln | Lys | Ile | Asp | Glu | Ser | Lys | Leu |
| | | | | 725 | | | | | 730 | | | | | 735 | |
| Lys | Ala | Tyr | Thr | Arg | Tyr | Glu | Leu | Arg | Gly | Tyr | Ile | Glu | Asp | Ser | Gln |
| | | | 740 | | | | | 745 | | | | | 750 | | |
| Asp | Leu | Glu | Ile | Tyr | Leu | Ile | Arg | Tyr | Asn | Ala | Lys | His | Glu | Thr | Val |
| | | 755 | | | | | 760 | | | | | 765 | | | |
| Asn | Val | Pro | Gly | Thr | Gly | Ser | Leu | Trp | Pro | Leu | Ser | Ala | Gln | Ser | Pro |
| | 770 | | | | | 775 | | | | | 780 | | | | |
| Ile | Gly | Lys | Cys | Gly | Glu | Pro | Asn | Arg | Cys | Ala | Pro | His | Leu | Glu | Trp |
| 785 | | | | | 790 | | | | | 795 | | | | | 800 |
| Asn | Pro | Asn | Leu | Asp | Cys | Ser | Cys | Arg | Asp | Gly | Glu | Lys | Cys | Ala | His |
| | | | | 805 | | | | | 810 | | | | | 815 | |
| His | Ser | His | His | Phe | Ser | Leu | Asp | Ile | Asp | Val | Gly | Cys | Thr | Asp | Leu |
| | | | 820 | | | | | 825 | | | | | 830 | | |
| Asn | Glu | Asp | Leu | Gly | Val | Trp | Val | Ile | Phe | Lys | Ile | Lys | Thr | Gln | Asp |
| | | 835 | | | | | 840 | | | | | 845 | | | |
| Gly | Tyr | Ala | Arg | Leu | Gly | Asn | Leu | Glu | Phe | Leu | Glu | Glu | Lys | Pro | Leu |
| | 850 | | | | | 855 | | | | | 860 | | | | |
| Leu | Gly | Glu | Ala | Leu | Ala | Arg | Val | Lys | Arg | Ala | Glu | Lys | Lys | Trp | Arg |
| 865 | | | | | 870 | | | | | 875 | | | | | 880 |
| Asp | Lys | Cys | Glu | Lys | Leu | Glu | Trp | Glu | Thr | Asn | Ile | Val | Tyr | Lys | Glu |
| | | | | 885 | | | | | 890 | | | | | 895 | |
| Ala | Lys | Glu | Ser | Val | Asp | Ala | Leu | Phe | Val | Asn | Ser | Gln | Tyr | Asp | Arg |
| | | | 900 | | | | | 905 | | | | | 910 | | |
| Leu | Gln | Ala | Asp | Thr | Asn | Ile | Ala | Met | Ile | His | Ala | Ala | Asp | Lys | Arg |
| | | 915 | | | | | 920 | | | | | 925 | | | |
| Val | His | Ser | Ile | Arg | Glu | Ala | Tyr | Leu | Pro | Glu | Leu | Ser | Val | Ile | Pro |
| | 930 | | | | | 935 | | | | | 940 | | | | |
| Gly | Val | Asn | Ala | Ala | Ile | Phe | Glu | Glu | Leu | Glu | Gly | Arg | Ile | Phe | Thr |
| 945 | | | | | 950 | | | | | 955 | | | | | 960 |
| Ala | Phe | Ser | Leu | Tyr | Asp | Ala | Arg | Asn | Val | Ile | Lys | Asn | Gly | Asp | Phe |
| | | | | 965 | | | | | 970 | | | | | 975 | |
| Asn | Asn | Gly | Leu | Ser | Cys | Trp | Asn | Val | Lys | Gly | His | Val | Asp | Val | Glu |
| | | | 980 | | | | | 985 | | | | | 990 | | |
| Glu | Gln | Asn | Asn | His | Arg | Ser | Val | Leu | Val | Val | Pro | Glu | Trp | Glu | Ala |
| | | 995 | | | | | 1000 | | | | | 1005 | | | |
| Glu | Val | Ser | Gln | Glu | Val | Arg | Val | Cys | Pro | Gly | Arg | Gly | Tyr | Ile | Leu |
| | 1010 | | | | | 1015 | | | | | 1020 | | | | |
| Arg | Val | Thr | Ala | Tyr | Lys | Glu | Gly | Tyr | Gly | Glu | Gly | Cys | Val | Thr | Ile |
| 1025 | | | | | 1030 | | | | | 1035 | | | | | 1040 |

-continued

His Glu Ile Glu Asp Asn Thr Asp Glu Leu Lys Phe Ser Asn Cys Val
1045 1050 1055

Glu Glu Glu Val Tyr Pro Asn Asn Thr Val Thr Cys Asn Asn Tyr Thr
1060 1065 1070

Ala Thr Gln Glu Glu His Glu Gly Thr Tyr Thr Ser Arg Asn Arg Gly
1075 1080 1085

Tyr Asp Glu Ala Tyr Glu Ser Asn Ser Ser Val His Ala Ser Val Tyr
1090 1095 1100

Glu Glu Lys Ser Tyr Thr Asp Arg Arg Arg Glu Asn Pro Cys Glu Ser
1105 1110 1115 1120

Asn Arg Gly Tyr Gly Asp Tyr Thr Pro Leu Pro Ala Gly Tyr Val Thr
1125 1130 1135

Lys Glu Leu Glu Tyr Phe Pro Glu Thr Asp Lys Val Trp Ile Glu Ile
1140 1145 1150

Gly Glu Thr Glu Gly Thr Phe Ile Val Asp Ser Val Glu Leu Leu Leu
1155 1160 1165

Met Glu Glu
1170

( 2 ) INFORMATION FOR SEQ ID NO:7:

( i ) SEQUENCE CHARACTERISTICS:
( A ) LENGTH: 3531 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: BACILLUS THURINGIENSIS
( B ) STRAIN: KURSTAKI
( C ) INDIVIDUAL ISOLATE: PS81GG ( v i i ) IMMEDIATE SOURCE:
( A ) LIBRARY: LAMBDAGEM (TM) - 11 LIBRARY OF AUGUST SICK
( B ) CLONE: 81GG ( x i ) SEQUENCE DESCRIPTION: SEQ ID NO:7:

ATGGATAACA ATCCGAACAT CAATGAATGC ATTCCTTATA ATTGTTTAAG TAACCCTGAA 60

GTAGAAGTAT TAGGTGGAGA AAGAATAGAA ACTGGTTACA CCCCAATCGA TATTTCCTTG 120

TCGCTAACGC AATTTCTTTT GAGTGAATTT GTTCCCGGTG CTGGATTTGT GTTAGGACTA 180

GTTGATATAA TATGGGGAAT TTTTGGTCCC TCTCAATGGG ACGCATTTCT TGTACAAATT 240

GAACAGTTAA TTAACCAAAG AATAGAAGAA TTCGCTAGGA ACCAAGCCAT TTCTAGATTA 300

GAAGGACTAA GCAATCTTTA TCAAATTTAC GCAGAATCTT TTAGAGAGTG GGAAGCAGAT 360

CCTACTAATC CAGCATTAAG AGAAGAGATG CGTATTCAAT TCAATGACAT GAACAGTGCC 420

CTTACAACCG CTATTCCTCT TTTGGCAGTT CAAAATTATC AAGTTCCTCT TTTATCAGTA 480

TATGTTCAAG CTGCAAATTT ACATTTATCA GTTTTGAGAG ATGTTTCAGT GTTTGGACAA 540

AGGTGGGGAT TTGATGCCGC GACTATCAAT AGTCGTTATA ATGATTTAAC TAGGCTTATT 600

GGCAACTATA CAGATTATGC TGTACGCTGG TACAATACGG GATTAGAACG TGTATGGGGA 660

CCGGATTCTA GAGATTGGGT AAGGTATAAT CAATTTAGAA GAGAATTAAC ACTAACTGTA 720

TTAGATATCG TTGCTCTGTT CCCGAATTAT GATAGTAGAA GATATCCAAT TCGAACAGTT 780

TCCCAATTAA CAAGAGAAAT TTATACAAAC CCAGTATTAG AAAATTTTGA TGGTAGTTTT 840

CGAGGCTCGG CTCAGGGCAT AGAAAGAAGT ATTAGGAGTC CACATTTGAT GGATATACTT 900

```
AACAGTATAA CCATCTATAC GGATGCTCAT AGGGGTTATT ATTATTGGTC AGGGCATCAA    960
ATAATGGCTT CTCCTGTCGG TTTTTCGGGG CCAGAATTCA CGTTTCCGCT ATATGGAACC   1020
ATGGGAAATG CAGCTCCACA ACAACGTATT GTTGCTCAAC TAGGTCAGGG CGTGTATAGA   1080
ACATTATCCT CTACTTTTTA TAGAAGACCT TTTAATATAG GGATAAATAA TCAACAACTA   1140
TCTGTTCTTG ACGGGACAGA ATTTGCTTAT GGAACCTCCT CAAATTTGCC ATCCGCTGTA   1200
TACAGAAAAA GCGGAACGGT AGATTCGCTG GATGAAATAC CACCACAGAA TAACAACGTG   1260
CCACCTAGGC AAGGATTTAG TCATCGATTA AGCCATGTTT CAATGTTTCG TTCAGGCTCT   1320
AGTAGTAGTG TAAGTATAAT AAGAGCTCCT ATGTTCTCTT GGATACATCG TAGTGCTGAA   1380
TTTAATAATA TAATTGCATC GGATAGTATT ACTCAAATCC CTGCAGTGAA GGGAAACTTT   1440
CTTTTTAATG GTTCTGTAAT TTCAGGACCA GGATTTACTG GTGGGACTTA GTTAGATTA   1500
AATAGTAGTG GAAATAACAT TCAGAATAGA GGGTATATTG AAGTTCCAAT TCACTTCCCA   1560
TCGACATCTA CCAGATATCG AGTTCGTGTA CGGTATGCTT CTGTAACCCC GATTCACCTC   1620
AACGTTAATT GGGGTAATTC ATCCATTTTT TCCAATACAG TACCAGCTAC AGCTACGTCA   1680
TTAGATAATC TACAATCAAG TGATTTTGGT TATTTTGAAA GTGCCAATGC TTTTACATCT   1740
TCATTAGGTA ATATAGTAGG TGTTAGAAAT TTTAGTGGGA CTGCAGGAGT GATAATAGAC   1800
AGATTTGAAT TTATTCCAGT TACTGCAACA CTCGAGGCTG AATATAATCT GGAAAGAGCG   1860
CAGAAGGCGG TGAATGCGCT GTTTACGTCT ACAAACCAAC TAGGGCTAAA AACAAATGTA   1920
ACGGATTATC ATATTGATCA AGTGTCCAAT TTAGTTACGT ATTTATCGGA TGAATTTTGT   1980
CTGGATGAAA AGCGAGAATT GTCCGAGAAA GTCAAACATG CGAAGCGACT CAGTGATGAA   2040
CGCAATTTAC TCCAAGATTC AAATTTCAAA GACATTAATA GGCAACCAGA ACGTGGGTGG   2100
GGCGGAAGTA CAGGGATTAC CATCCAAGGA GGGGATGACG TATTTAAAGA AAATTACGTC   2160
ACACTATCAG GTACCTTTGA TGAGTGCTAT CCAACATATT TGTATCAAAA AATCGATGAA   2220
TCAAAATTAA AAGCCTTTAC CCGTTATCAA TTAAGAGGGT ATATCGAAGA TAGTCAAGAC   2280
TTAGAAATCT ATTTAATTCG CTACAATGCA AAACATGAAA CAGTAAATGT GCCAGGTACG   2340
GGTTCCTTAT GGCCGCTTTC AGCCCAAAGT CCAATCGGAA AGTGTGGAGA GCCGAATCGA   2400
TGCGCGCCAC ACCTTGAATG GAATCCTGAC TTAGATTGTT CGTGTAGGGA TGGAGAAAAG   2460
TGTGCCCATC ATTCGCATCA TTTCTCCTTA GACATTGATG TAGGATGTAC AGACTTAAAT   2520
GAGGACCTAG GTGTATGGGT GATCTTTAAG ATTAAGACGC AAGATGGGCA CGCAAGACTA   2580
GGGAATCTAG AGTTTCTCGA AGAGAAACCA TTAGTAGGAG AAGCGCTAGC TCGTGTGAAA   2640
AGAGCGGAGA AAAATGGAG AGACAAACGT GAAAATTGG AATGGGAAAC AAATATCGTT   2700
TATAAAGAGG CAAAAGAATC TGTAGATGCT TTATTTGTAA ACTCTCAATA TGATCAATTA   2760
CAAGCGGATA CGAATATTGC CATGATTCAT GCGGCAGATA AACGTGTTCA TAGCATTCGA   2820
GAAGCTTATC TGCCTGAGCT GTCTGTGATT CCGGGTGTCA ATGCGGCTAT TTTTGAAGAA   2880
TTAGAAGGGC GTATTTTCAC TGCATTCTCC CTATATGATG CGAGAAATGT CATTAAAAAT   2940
GGTGATTTTA ATAATGGCTT ATCCTGCTGG AACGTGAAAG GGCATGTAGA TGTAGAAGAA   3000
CAAAACAACC AACGTTCGGT CCTTGTTGTT CCGGAATGGG AAGCAGAAGT GTCACAAGAA   3060
GTTCGTGTCT GTCCGGGTCG TGGCTATATC CTTCGTGTCA CAGCGTACAA GGAGGGATAT   3120
GGAGAAGGTT GCGTAACCAT TCATGAGATC GAGAACAATA CAGACGAACT GAAGTTTAGC   3180
AACTGCGTAG AAGAGGAAAT CTATCCAAAT AACACGGTAA CGTGTAATGA TTATACTGTA   3240
AATCAAGAAG AATACGGAGG TGCGTACACT TCTCGTAATC GAGGATATAA CGAAGCTCCT   3300
TCCGTACCAG CTGATTATGC GTCAGTCTAT GAAGAAAAAT CGTATACAGA TGGACGAAGA   3360
```

```
GAGAATCCTT GTGAATTTAA CAGAGGGTAT AGGGATTACA CGCCACTACC AGTTGGTTAT    3420

GTGACAAAAG AATTAGAATA CTTCCCAGAA ACCGATAAGG TATGGATTGA GATTGGAGAA    3480

ACGGAAGGAA CATTTATCGT GGACAGCGTG GAATTACTCC TTATGGAGGA A             3531
```

( 2 ) INFORMATION FOR SEQ ID NO:8:

( i ) SEQUENCE CHARACTERISTICS:
        ( A ) LENGTH: 1177 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
        ( A ) ORGANISM: BACILLUS THURINGIENSIS
        ( B ) STRAIN: KURSTAKI
        ( C ) INDIVIDUAL ISOLATE: PS81GG ( v i i ) IMMEDIATE SOURCE:
        ( A ) LIBRARY: LAMBDAGEM (TM) - 11 LIBRARY OF AUGUST SICK
        ( B ) CLONE: 81GG ( x i ) SEQUENCE DESCRIPTION: SEQ ID NO:8:

```
Met Asp Asn Asn Pro Asn Ile Asn Glu Cys Ile Pro Tyr Asn Cys Leu
 1               5                  10                 15

Ser Asn Pro Glu Val Glu Val Leu Gly Gly Glu Arg Ile Glu Thr Gly
            20                  25                 30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
```

-continued

|     |     |     | 260 |     |     |     | 265 |     |     |     | 270 |     |     |
|---|---|---|---|---|---|---|---|---|---|---|---|---|---|

Leu Glu Asn Phe Asp Gly Ser Phe Arg Gly Ser Ala Gln Gly Ile Glu
        275                280               285

Arg Ser Ile Arg Ser Pro His Leu Met Asp Ile Leu Asn Ser Ile Thr
    290                295              300

Ile Tyr Thr Asp Ala His Arg Gly Tyr Tyr Tyr Trp Ser Gly His Gln
305              310            315           320

Ile Met Ala Ser Pro Val Gly Phe Ser Gly Pro Glu Phe Thr Phe Pro
            325            330             335

Leu Tyr Gly Thr Met Gly Asn Ala Ala Pro Gln Gln Arg Ile Val Ala
            340            345           350

Gln Leu Gly Gln Gly Val Tyr Arg Thr Leu Ser Ser Thr Phe Tyr Arg
        355              360           365

Arg Pro Phe Asn Ile Gly Ile Asn Asn Gln Gln Leu Ser Val Leu Asp
370              375            380

Gly Thr Glu Phe Ala Tyr Gly Thr Ser Ser Asn Leu Pro Ser Ala Val
385              390            395           400

Tyr Arg Lys Ser Gly Thr Val Asp Ser Leu Asp Glu Ile Pro Pro Gln
            405            410           415

Asn Asn Asn Val Pro Pro Arg Gln Gly Phe Ser His Arg Leu Ser His
        420              425           430

Val Ser Met Phe Arg Ser Gly Ser Ser Ser Val Ser Ile Ile Arg
        435              440           445

Ala Pro Met Phe Ser Trp Ile His Arg Ser Ala Glu Phe Asn Asn Ile
    450                455           460

Ile Ala Ser Asp Ser Ile Thr Gln Ile Pro Ala Val Lys Gly Asn Phe
465              470            475           480

Leu Phe Asn Gly Ser Val Ile Ser Gly Pro Gly Phe Thr Gly Gly Asp
              485            490           495

Leu Val Arg Leu Asn Ser Ser Gly Asn Asn Ile Gln Asn Arg Gly Tyr
            500            505           510

Ile Glu Val Pro Ile His Phe Pro Ser Thr Ser Thr Arg Tyr Arg Val
        515              520           525

Arg Val Arg Tyr Ala Ser Val Thr Pro Ile His Leu Asn Val Asn Trp
    530                535           540

Gly Asn Ser Ser Ile Phe Ser Asn Thr Val Pro Ala Thr Ala Thr Ser
545              550            555           560

Leu Asp Asn Leu Gln Ser Ser Asp Phe Gly Tyr Phe Glu Ser Ala Asn
            565            570           575

Ala Phe Thr Ser Ser Leu Gly Asn Ile Val Gly Val Arg Asn Phe Ser
            580            585           590

Gly Thr Ala Gly Val Ile Ile Asp Arg Phe Glu Phe Ile Pro Val Thr
        595              600           605

Ala Thr Leu Glu Ala Glu Tyr Asn Leu Glu Arg Ala Gln Lys Ala Val
610              615            620

Asn Ala Leu Phe Thr Ser Thr Asn Gln Leu Gly Leu Lys Thr Asn Val
625              630            635           640

Thr Asp Tyr His Ile Asp Gln Val Ser Asn Leu Val Thr Tyr Leu Ser
              645            650           655

Asp Glu Phe Cys Leu Asp Glu Lys Arg Glu Leu Ser Glu Lys Val Lys
            660            665           670

His Ala Lys Arg Leu Ser Asp Glu Arg Asn Leu Leu Gln Asp Ser Asn
        675              680           685

Phe Lys Asp Ile Asn Arg Gln Pro Glu Arg Gly Trp Gly Gly Ser Thr
    690                695           700

```
Gly Ile Thr Ile Gln Gly Gly Asp Asp Val Phe Lys Glu Asn Tyr Val
705                 710             715                 720

Thr Leu Ser Gly Thr Phe Asp Glu Cys Tyr Pro Thr Tyr Leu Tyr Gln
            725             730                     735

Lys Ile Asp Glu Ser Lys Leu Lys Ala Phe Thr Arg Tyr Gln Leu Arg
            740             745                 750

Gly Tyr Ile Glu Asp Ser Gln Asp Leu Glu Ile Tyr Leu Ile Arg Tyr
        755             760             765

Asn Ala Lys His Glu Thr Val Asn Val Pro Gly Thr Gly Ser Leu Trp
        770             775             780

Pro Leu Ser Ala Gln Ser Pro Ile Gly Lys Cys Gly Glu Pro Asn Arg
785             790             795                         800

Cys Ala Pro His Leu Glu Trp Asn Pro Asp Leu Asp Cys Ser Cys Arg
                805             810                 815

Asp Gly Glu Lys Cys Ala His His Ser His His Phe Ser Leu Asp Ile
            820             825                 830

Asp Val Gly Cys Thr Asp Leu Asn Glu Asp Leu Gly Val Trp Val Ile
        835             840             845

Phe Lys Ile Lys Thr Gln Asp Gly His Ala Arg Leu Gly Asn Leu Glu
    850             855             860

Phe Leu Glu Glu Lys Pro Leu Val Gly Glu Ala Leu Ala Arg Val Lys
865             870             875                         880

Arg Ala Glu Lys Lys Trp Arg Asp Lys Arg Glu Lys Leu Glu Trp Glu
            885             890                     895

Thr Asn Ile Val Tyr Lys Glu Ala Lys Glu Ser Val Asp Ala Leu Phe
        900             905                 910

Val Asn Ser Gln Tyr Asp Gln Leu Gln Ala Asp Thr Asn Ile Ala Met
        915             920             925

Ile His Ala Ala Asp Lys Arg Val His Ser Ile Arg Glu Ala Tyr Leu
930             935                 940         ,

Pro Glu Leu Ser Val Ile Pro Gly Val Asn Ala Ala Ile Phe Glu Glu
945             950             955                         960

Leu Glu Gly Arg Ile Phe Thr Ala Phe Ser Leu Tyr Asp Ala Arg Asn
            965             970                     975

Val Ile Lys Asn Gly Asp Phe Asn Asn Gly Leu Ser Cys Trp Asn Val
        980             985                 990

Lys Gly His Val Asp Val Glu Glu Gln Asn Asn Gln Arg Ser Val Leu
        995             1000            1005

Val Val Pro Glu Trp Glu Ala Glu Val Ser Gln Glu Val Arg Val Cys
    1010            1015                1020

Pro Gly Arg Gly Tyr Ile Leu Arg Val Thr Ala Tyr Lys Glu Gly Tyr
1025            1030                1035                1040

Gly Glu Gly Cys Val Thr Ile His Glu Ile Glu Asn Asn Thr Asp Glu
            1045            1050                    1055

Leu Lys Phe Ser Asn Cys Val Glu Glu Glu Ile Tyr Pro Asn Asn Thr
            1060            1065                1070

Val Thr Cys Asn Asp Tyr Thr Val Asn Gln Glu Glu Tyr Gly Gly Ala
        1075            1080                1085

Tyr Thr Ser Arg Asn Arg Gly Tyr Asn Glu Ala Pro Ser Val Pro Ala
        1090            1095                1100

Asp Tyr Ala Ser Val Tyr Glu Glu Lys Ser Tyr Thr Asp Gly Arg Arg
1105            1110            1115                        1120

Glu Asn Pro Cys Glu Phe Asn Arg Gly Tyr Arg Asp Tyr Thr Pro Leu
            1125            1130                1135
```

|  | Pro | Val | Gly | Tyr<br>1140 | Val | Thr | Lys | Glu | Leu<br>1145 | Glu | Tyr | Phe | Pro | Glu<br>1150 | Thr | Asp |
| --- | --- | --- | --- | --- | --- | --- | --- | --- | --- | --- | --- | --- | --- | --- | --- | --- |
|  | Lys | Val | Trp | Ile<br>1155 | Glu | Ile | Gly | Glu | Thr<br>1160 | Glu | Gly | Thr | Phe | Ile<br>1165 | Val | Asp |
|  | Ser | Val | Glu | Leu<br>1170 | Leu | Leu | Met | Glu | Glu<br>1175 |  |  |  |  |  |  |  |

( 2 ) INFORMATION FOR SEQ ID NO:9:

( i ) SEQUENCE CHARACTERISTICS:
        ( A ) LENGTH: 3522 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: BACILLUS THURINGIENSIS
        ( B ) STRAIN: AIZAWAI
        ( C ) INDIVIDUAL ISOLATE: PS81I ( v i i ) IMMEDIATE SOURCE:
        ( A ) LIBRARY: LAMBDAGEM (TM) - 11 LIBRARY OF AUGUST SICK
        ( B ) CLONE: 81IA ( x i ) SEQUENCE DESCRIPTION: SEQ ID NO:9:

```
ATGGAGAATA ATATTCAAAA TCAATGCGTA CCTTACAATT GTTTAAATAA TCCTGAAGTA        60
GAAATATTAA ATGAAGAAAG AAGTACTGGC AGATTACCGT TAGATATATC CTTATCGCTT       120
ACACGTTTCC TTTTGAGTGA ATTTGTTCCA GGTGTGGGAG TTGCGTTTGG ATTATTTGAT       180
TTAATATGGG GTTTTATAAC TCCTTCTGAT TGGAGCTTAT TTCTTTTACA GATTGAACAA       240
TTGATTGAGC AAAGAATAGA AACATTGGAA AGGAACCGGG CAATTACTAC ATTACGAGGG       300
TTAGCAGATA GCTATGAAAT TTATATTGAA GCACTAAGAG AGTGGGAAGC AAATCCTAAT       360
AATGCACAAT TAAGGGAAGA TGTGCGTATT CGATTTGCTA ATACAGACGA CGCTTTAATA       420
ACAGCAATAA ATAATTTTAC ACTTACAAGT TTTGAAATCC CTCTTTTATC GGTCTATGTT       480
CAAGCGGCGA ATTTACATTT ATCACTATTA AGAGACGCTG TATCGTTTGG GCAGGGTTGG       540
GGACTGGATA TAGCTACTGT TAATAATCAT TATAATAGAT TAATAAATCT TATTCATAGA       600
TATACGAAAC ATTGTTTGGA CACATACAAT CAAGGATTAG AAAACTTAAG AGGTACTAAT       660
ACTCGACAAT GGGCAAGATT CAATCAGTTT AGGAGAGATT TAACACTTAC TGTATTAGAT       720
ATCGTTGCTC TTTTTCCGAA CTACGATGTT AGAACATATC CAATTCAAAC GTCATCCCAA       780
TTAACAAGGG AAATTTATAC AAGTTCAGTA ATTGAGGATT CTCCAGTTTC TGCTAATATA       840
CCTAATGGTT TTAATAGGGC GGAATTTGGA GTTAGACCGC CCCATCTTAT GGACTTTATG       900
AATTCTTTGT TTGTAACTGC AGAGACTGTT AGAAGTCAAA CTGTGTGGGG AGGACACTTA       960
GTTAGTTCAC GAAATACGGC TGGTAACCGT ATAAATTTCC CTAGTTACGG GGTCTTCAAT      1020
CCTGGTGGCG CCATTTGGAT TGCAGATGAG GATCCACGTC CTTTTATCG GACATTATCA      1080
GATCCTGTTT TTGTCCGAGG AGGATTTGGG AATCCTCATT ATGTACTGGG GCTTAGGGGA     1140
GTAGCATTTC AACAAACTGG TACGAACCAC ACCCGAACAT TTAGAAATAG TGGGACCATA     1200
GATTCTCTAG ATGAAATCCC ACCTCAGGAT AATAGTGGGG CACCTTGGAA TGATTATAGT     1260
CATGTATTAA ATCATGTTAC ATTTGTACGA TGGCCAGGTG AGATTTCAGG AAGTGATTCA     1320
TGGAGAGCTC CAATGTTTTC TTGGACGCAC CGTAGTGCAA CCCCTACAAA TACAATTGAT     1380
CCGGAGAGGA TTACTCAAAT ACCATTGGTA AAAGCACATA CACTTCAGTC AGGTACTACT     1440
```

```
GTTGTAAGAG GGCCCGGGTT TACGGGAGGA GATATTCTTC GACGAACAAG TGGAGGACCA    1500
TTTGCTTATA CTATTGTTAA TATAAATGGG CAATTACCCC AAAGGTATCG TGCAAGAATA    1560
CGCTATGCCT CTACTACAAA TCTAAGAATT TACGTAACGG TTGCAGGTGA ACGGATTTTT    1620
GCTGGTCAAT TTAACAAAAC AATGGATACC GGTGACCCAT TAACATTCCA ATCTTTTAGT    1680
TACGCAACTA TTAATACAGC TTTTACATTC CCAATGAGCC AGAGTAGTTT CACAGTAGGT    1740
GCTGATACTT TTAGTTCAGG GAATGAAGTT TATATAGACA GATTTGAATT GATTCCAGTT    1800
ACTGCAACAT TTGAAGCAGA ATATGATTTA GAAAGAGCAC AAAAGGCGGT GAATGCGCTG    1860
TTTACTTCTA TAAACCAAAT AGGGATAAAA ACAGATGTGA CGGATTATCA TATTGATCAA    1920
GTATCCAATT TAGTGGATTG TTTATCAGAT GAATTTGTC TGGATGAAAA GCGAGAATTG     1980
TCCGAGAAAG TCAAACATGC GAAGCGACTC AGTGATGAGC GGAATTTACT TCAAGATCCA    2040
AACTTCAAAG GCATCAATAG GCAACTAGAC CGTGGTTGGA GAGGAAGTAC GGATATTACC    2100
ATCCAAAGAG GAGATGACGT ATTCAAAGAA AATTATGTCA CACTACCAGG TACCTTTGAT    2160
GAGTGCTATC CAACGTATTT ATATCAAAAA ATAGATGAGT CGAAATTAAA ACCCTATACT    2220
CGTTATCAAT TAAGAGGGTA TATCGAGGAT AGTCAAGACT TAGAAATCTA TTTGATCCGC    2280
TATAATGCAA AACACGAAAC AGTAAATGTG CTAGGTACGG GTTCTTTATG GCCGCTTTCA    2340
GTCCAAAGTC CAATCAGAAA GTGTGGAGAA CCGAATCGAT GCGCGCCACA CCTTGAATGG    2400
AATCCTGATC TAGATTGTTC CTGCAGAGAC GGGGAAAAAT GTGCACATCA TTCGCATCAT    2460
TTCTCCTTGG ACATTGATGT TGGATGTACA GACTTAAATG AGGACTTAGA TGTATGGGTG    2520
ATATTCAAGA TTAAGACGCA AGATGGCCAT GCAAGACTAG GAAATCTAGA GTTTCTCGAA    2580
GAGAAACCAT TAGTCGGGGA AGCACTAGCT CGTGTGAAAA GAGCAGAGAA AAAATGGAGA    2640
GATAAACGTG AAAAATTGGA ATTGGAAACA ATATTGTTT ATAAAGAGGC AAAAGAATCT     2700
GTAGATGCTT TATTTGTAAA CTCTCAATAT GATCAATTAC AAGCGGATAC GAATATTGCC    2760
ATGATTCATG CGGCAGATAA ACGTGTTCAT AGAATTCGGG AAGCGTATCT TCCAGAGTTA    2820
TCTGTGATTC CGGGTGTAAA TGTAGACATT TTCGAAGAAT TAAAAGGGCG TATTTTCACT    2880
GCATTCTTCC TATATGATGC GAGAAATGTC ATTAAAAACG GTGATTTCAA TAATGGCTTA    2940
TCATGCTGGA ACGTGAAAGG GCATGTAGAT GTAGAAGAAC AAAACAACCA CCGTTCGGTC    3000
CTTGTTGTTC CGGAATGGGA AGCAGAAGTG TCACAAGAAG TTCGTGTCTG TCCGGGTCGT    3060
GGCTATATCC TTCGTGTCAC AGCGTACAAG GAGGGATATG GAGAAGGTTG CGTAACCATT    3120
CATGAGATCG AGAACAATAC AGACGAACTG AAGTTTAGCA ACTGCGTAGA AGAGGAAGTC    3180
TATCCAAACA ACACGGTAAC GTGTAATGAT TATACTGCAA ATCAAGAAGA ATACGGGGGT    3240
GCGTACACTT CCCGTAATCG TGGATATGAC GAAACTTATG GAAGCAATTC TTCTGTACCA    3300
GCTGATTATG CGTCAGTCTA TGAAGAAAAA TCGTATACAG ATGGACGAAG AGACAATCCT    3360
TGTGAATCTA ACAGAGGATA TGGGGATTAC ACACCACTAC CAGCTGGCTA TGTGACAAAA    3420
GAATTAGAGT ACTTCCCAGA AACCGATAAG GTATGGATTG AGATCGGAGA AACGGAAGGA    3480
ACATTCATCG TGGACAGCGT GGAATTACTC CTTATGGAGG AA                       3522
```

( 2 ) INFORMATION FOR SEQ ID NO:10:

( i ) SEQUENCE CHARACTERISTICS:
        ( A ) LENGTH: 1174 amino acids
        ( B ) TYPE: amino acid
        ( C ) STRANDEDNESS: single
        ( D ) TOPOLOGY: linear ( i i ) MOLECULE TYPE: protein (iii) HYPOTHETICAL: YES (iv) ANTI-SENSE: NO (vi) ORIGINAL SOURCE:
    (A) ORGANISM: BACILLUS THURINGIENSIS
    (B) STRAIN: AIZAWAI
    (C) INDIVIDUAL ISOLATE: PS81I (vii) I -continued

|     |     |     | 355 |     |     |     | 360 |     |     |     | 365 |     |     |     |
|-----|-----|-----|-----|-----|-----|-----|-----|-----|-----|-----|-----|-----|-----|-----|

Phe Gly Asn Pro His Tyr Val Leu Gly Leu Arg Gly Val Ala Phe Gln
370                     375                 380

Gln Thr Gly Thr Asn His Thr Arg Thr Phe Arg Asn Ser Gly Thr Ile
385                 390                 395                 400

Asp Ser Leu Asp Glu Ile Pro Pro Gln Asp Asn Ser Gly Ala Pro Trp
                    405                 410                 415

Asn Asp Tyr Ser His Val Leu Asn His Val Thr Phe Val Arg Trp Pro
                420                 425                 430

Gly Glu Ile Ser Gly Ser Asp Ser Trp Arg Ala Pro Met Phe Ser Trp
            435                 440                 445

Thr His Arg Ser Ala Thr Pro Thr Asn Thr Ile Asp Pro Glu Arg Ile
450                 455                 460

Thr Gln Ile Pro Leu Val Lys Ala His Thr Leu Gln Ser Gly Thr Thr
465                 470                 475                 480

Val Val Arg Gly Pro Gly Phe Thr Gly Gly Asp Ile Leu Arg Arg Thr
                485                 490                 495

Ser Gly Gly Pro Phe Ala Tyr Thr Ile Val Asn Ile Asn Gly Gln Leu
                500                 505                 510

Pro Gln Arg Tyr Arg Ala Arg Ile Arg Tyr Ala Ser Thr Thr Asn Leu
            515                 520                 525

Arg Ile Tyr Val Thr Val Ala Gly Glu Arg Ile Phe Ala Gly Gln Phe
530                 535                 540

Asn Lys Thr Met Asp Thr Gly Asp Pro Leu Thr Phe Gln Ser Phe Ser
545                 550                 555                 560

Tyr Ala Thr Ile Asn Thr Ala Phe Thr Phe Pro Met Ser Gln Ser Ser
                565                 570                 575

Phe Thr Val Gly Ala Asp Thr Phe Ser Ser Gly Asn Glu Val Tyr Ile
            580                 585                 590

Asp Arg Phe Glu Leu Ile Pro Val Thr Ala Thr Phe Glu Ala Glu Tyr
        595                 600                 605

Asp Leu Glu Arg Ala Gln Lys Ala Val Asn Ala Leu Phe Thr Ser Ile
    610                 615                 620

Asn Gln Ile Gly Ile Lys Thr Asp Val Thr Asp Tyr His Ile Asp Gln
625                 630                 635                 640

Val Ser Asn Leu Val Asp Cys Leu Ser Asp Glu Phe Cys Leu Asp Glu
                645                 650                 655

Lys Arg Glu Leu Ser Glu Lys Val Lys His Ala Lys Arg Leu Ser Asp
            660                 665                 670

Glu Arg Asn Leu Leu Gln Asp Pro Asn Phe Lys Gly Ile Asn Arg Gln
        675                 680                 685

Leu Asp Arg Gly Trp Arg Gly Ser Thr Asp Ile Thr Ile Gln Arg Gly
    690                 695                 700

Asp Asp Val Phe Lys Glu Asn Tyr Val Thr Leu Pro Gly Thr Phe Asp
705                 710                 715                 720

Glu Cys Tyr Pro Thr Tyr Leu Tyr Gln Lys Ile Asp Glu Ser Lys Leu
                725                 730                 735

Lys Pro Tyr Thr Arg Tyr Gln Leu Arg Gly Tyr Ile Glu Asp Ser Gln
            740                 745                 750

Asp Leu Glu Ile Tyr Leu Ile Arg Tyr Asn Ala Lys His Glu Thr Val
        755                 760                 765

Asn Val Leu Gly Thr Gly Ser Leu Trp Pro Leu Ser Val Gln Ser Pro
    770                 775                 780

Ile Arg Lys Cys Gly Glu Pro Asn Arg Cys Ala Pro His Leu Glu Trp
785                 790                 795                 800

```
Asn Pro Asp Leu Asp Cys Ser Cys Arg Asp Gly Glu Lys Cys Ala His
            805                 810                 815
His Ser His His Phe Ser Leu Asp Ile Asp Val Gly Cys Thr Asp Leu
            820                 825                 830
Asn Glu Asp Leu Asp Val Trp Val Ile Phe Lys Ile Lys Thr Gln Asp
            835                 840                 845
Gly His Ala Arg Leu Gly Asn Leu Glu Phe Leu Glu Glu Lys Pro Leu
            850                 855                 860
Val Gly Glu Ala Leu Ala Arg Val Lys Arg Ala Glu Lys Lys Trp Arg
865                 870                 875                 880
Asp Lys Arg Glu Lys Leu Glu Leu Glu Thr Asn Ile Val Tyr Lys Glu
                885                 890                 895
Ala Lys Glu Ser Val Asp Ala Leu Phe Val Asn Ser Gln Tyr Asp Gln
            900                 905                 910
Leu Gln Ala Asp Thr Asn Ile Ala Met Ile His Ala Ala Asp Lys Arg
            915                 920                 925
Val His Arg Ile Arg Glu Ala Tyr Leu Pro Glu Leu Ser Val Ile Pro
            930                 935                 940
Gly Val Asn Val Asp Ile Phe Glu Glu Leu Lys Gly Arg Ile Phe Thr
945                 950                 955                 960
Ala Phe Phe Leu Tyr Asp Ala Arg Asn Val Ile Lys Asn Gly Asp Phe
            965                 970                 975
Asn Asn Gly Leu Ser Cys Trp Asn Val Lys Gly His Val Asp Val Glu
            980                 985                 990
Glu Gln Asn Asn His Arg Ser Val Leu Val Val Pro Glu Trp Glu Ala
            995                 1000                1005
Glu Val Ser Gln Glu Val Arg Val Cys Pro Gly Arg Gly Tyr Ile Leu
            1010                1015                1020
Arg Val Thr Ala Tyr Lys Glu Gly Tyr Gly Glu Gly Cys Val Thr Ile
1025                1030                1035                1040
His Glu Ile Glu Asn Asn Thr Asp Glu Leu Lys Phe Ser Asn Cys Val
                1045                1050                1055
Glu Glu Glu Val Tyr Pro Asn Asn Thr Val Thr Cys Asn Asp Tyr Thr
            1060                1065                1070
Ala Asn Gln Glu Glu Tyr Gly Gly Ala Tyr Thr Ser Arg Asn Arg Gly
            1075                1080                1085
Tyr Asp Glu Thr Tyr Gly Ser Asn Ser Ser Val Pro Ala Asp Tyr Ala
            1090                1095                1100
Ser Val Tyr Glu Glu Lys Ser Tyr Thr Asp Gly Arg Arg Asp Asn Pro
1105                1110                1115                1120
Cys Glu Ser Asn Arg Gly Tyr Gly Asp Tyr Thr Pro Leu Pro Ala Gly
                1125                1130                1135
Tyr Val Thr Lys Glu Leu Glu Tyr Phe Pro Glu Thr Asp Lys Val Trp
            1140                1145                1150
Ile Glu Ile Gly Glu Thr Glu Gly Thr Phe Ile Val Asp Ser Val Glu
            1155                1160                1165
Leu Leu Leu Met Glu Glu
            1170
```

( 2 ) INFORMATION FOR SEQ ID NO:11:

( i ) SEQUENCE CHARACTERISTICS:
        ( A ) LENGTH: 3528 base pairs
        ( B ) TYPE: nucleic acid
        ( C ) STRANDEDNESS: double
        ( D ) TOPOLOGY: linear -continued ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: BACILLUS THURINGIENSIS
( B ) STRAIN: AIZAWAI
( C ) INDIVIDUAL ISOLATE: PS81I ( v i i ) IMMEDIATE SOURCE:
( A ) LIBRARY: LAMBDAGEM (TM) - 11 LIBRARY OF AUGUST SICK
( B ) CLONE: 81IA2

( x i ) SEQUENCE DESCRIPTION: SEQ ID NO:11:

```
ATGAATAATC AGAATCAATG CGTTCCTTAT AACTGTTTGA ATGATCCGAC AATTGAAATA   60
TTAGAAGGAG AAAGAATAGA AACTGGTTAC ACCCCAATAG ATATTTCCTT GTCGCTAACG  120
CAATTTCTGT TGAGTGAATT TGTCCCAGGT GCTGGGTTTG TATTAGGTTT AATTGATTTA  180
ATATGGGGGT TTGTGGGTCC CTCTCAATGG GATGCATTTC TTGTGCAAAT TGAACAGTTA  240
ATTAACCAAA GAATAGAGGA ATTCGCTAGG AACCAAGCAA TTTCTAGATT AGAAGGGCTA  300
AGCAACCTTT ATCAAATTTA CGCAGAAGCT TTTAGAGAGT GGGAAGCAGA TCCTACTAAT  360
CCAGCATTAA CAGAAGAGAT GCGTATTCAG TTCAATGACA TGAACAGTGC TCTTACAACC  420
GCTATTCCTC TTTTTACAGT TCAAAATTAT CAAGTACCTC TTCTATCAGT ATATGTTCAA  480
GCTGCAAATT TACATTTATC GGTTTTGAGA GATGTTTCAG TGTTTGGACA ACGTTGGGGA  540
TTTGATGTAG CAACAATCAA TAGTCGTTAT AATGATTTAA CTAGGCTTAT TGGCACCTAT  600
ACAGATTATG CTGTACGCTG GTATAATACG GGATTAGAAC GTGTATGGGG ACCGGATTCT  660
AGAGATTGGG TAAGGTATAA TCAATTTAGA AGAGAGCTAA CACTAACTGT ATTAGATATC  720
GTTTCTCTGT TCCCGAACTA TGATAGTAGA ACGTATCCAA TTCGAACAGT TTCCCAATTA  780
ACTAGAGAAA TTTATACAAA CCCAGTATTA GAAAATTTTG ATGGTAGTTT TCGTGGAATG  840
GCTCAGAGAA TAGAACAGAA TATTAGGCAA CCACATCTTA TGGATCTCCT TAATAGTATA  900
ACCATTTATA CTGATGTGCA TAGAGGCTTT AATTATTGGT CAGGACATCA AATAACAGCT  960
TCTCCTGTCG GTTTTGCGGG GCCAGAATTT ACTTTTCCTA GATATGGAAC CATGGGAAAT 1020
GCTGCTCCAC CCGTACTGAT CTCAACTACT GGTTTGGGGA TTTTTAGAAC ATTATCTTCA 1080
CCTCTTTACA GAAGAATTAT ACTTGGTTCA GGCCCAAATA ATCAGAACCT GTTTGTCCTT 1140
GATGGAACGG AATTTTCTTT TGCCTCCCTA ACAGCCGATT TACCTTCTAC TATATACAGA 1200
CAAAGGGGAA CGGTCGATTC ACTAGATGTA ATACCGCCAC AGGATAATAG TGTGCCAGCA 1260
CGTGCGGGAT TTAGTCATCG ATTAAGTCAT GTTACAATGC TGAGCCAAGC AGCTGGAGCA 1320
GTTTACACCT TGAGAGCTCC AACGTTTTCT TGGCGACATC GTAGTGCTGA ATTCTCTAAC 1380
CTAATTCCTT CATCACAAAT CACACAGATA CCTTTAACAA AGTCTATTAA TCTTGGCTCT 1440
GGGACCTCTG TTGTTAAAGG ACCAGGATTT ACAGGAGGAG ATATTCTTCG AATAACTTCA 1500
CCTGGCCAGA TTTCAACCTT AAGAGTGACT ATTACGGCAC CATTATCACA AAGATATCGC 1560
GTAAGAATTC GCTACGCTTC TACTACAAAT TTACAATTCC ATACATCAAT TGACGGAAGA 1620
CCTATTAATC AGGGGAATTT TTCAGCAACT ATGAGTAGTG GGGGTAATTT ACAGTCCGGA 1680
AGCTTTAGGA CTGCAGGTTT TACTACTCCG TTTAACTTTT CAAATGGATC AAGTATATTT 1740
ACGTTAAGTG CTCATGTCTT CAATTCAGGC AATGAAGTTT ATATAGAGCG AATTGAATTT 1800
GTTCCGGCAG AAGTAACATT TGAGGCGGAA TATGATTTAG AAAGAGCGCA AGAGGCGGTG 1860
AATGCTCTGT TTACTTCTTC CAATCAACTA GGATTAAAAA CAAATGTGAC GGACTATCAT 1920
ATTGATCAAG TGTCCAATCT AGTCGAATGT TTATCCGGTG AATTCTGTCT GGATGAAAAG 1980
```

-continued

```
AGAGAATTGT CCGAGAAAGT CAAACATGCG AACCGACTCA GTGATGAGCG GAATTTACTT   2040
CAAGACCCAA ACTTCAGAGG CATCAATAGA CAACCAGACC GTGGCTGGAG AGGCAGTACG   2100
GATATTACCA TCCAAGGAGG AGATGACGTA TTCAAAGAGA ATTACGTCAC ACTACCGGGT   2160
ACCTTTAATG AGTGTTATCC TACGTATCTG TATCAAAAAA TAGATGAGTC GAAATTAAAA   2220
GCCTATACCC GTTACCAATT AAGAGGGTAC ATCGAGGATA GTCAACACTT AGAAATCTAT   2280
TTAATTCGCT ACAATACAAA ACACGAAACA GTAAATGTGC CAGGTACGGG TTCCTTATGG   2340
CCGCTTTCAG TCGAAAATCC AATTGGAAAG TGCGGAGAAC CAAATCGATG CGCACCACAA   2400
CTTGAATGGA ATCCTGATCT AGATTGTTCC TGCAGAGACG GGGAAAAATG TGCACATCAC   2460
TCCCATCATT TCTCCTTGGA CATTGATATT GGATGTACAG ATTTAAATGA GAACTTAGGT   2520
GTATGGGTGA TATTCAAAAT TAAGATGCAA GATGGTCACG CAAGACTAGG TAATCTAGAG   2580
TTTCTCGAAG AGAAACCATT AGTAGGCGAA TCGTTAGCAC GCGTGAAGAG AGCGGAGAAG   2640
AAGTGGAGAG ACAAACGAGA GAAATTGCAA GTGGAAACAA ATATCGTTTA TAAAGAGGCA   2700
AAAGAATCTG TAGATGCTTT ATTTGTGAAC TCTCAATATG ATAGATTACA AGCGGATACC   2760
GACATCGCGA TGATTCATGC GGCAGATAAA CGCGTTCATC GAATTCGAGA AGCATATCTT   2820
CCAGAGTTAT CTGTAATTCC GGGTGTCAAT GCGGGCATTT TTGAAGAATT AGAGGGACGT   2880
ATTTTCACAG CCTACTCTTT ATATGATGCG AGAAATGTCA TTAAAAATGG CGATTTCAAT   2940
AATGGCTTAT CATGCTGGAA CGTGAAAGGG CATGTAGATG TAGAAGAACA AAACAACCAC   3000
CGTTCGGTTC TTGTTGTCCC GGAATGGGAA GCAGAGGTGT CACAAGAGGT TCGTGTCTGT   3060
CCAGGTCGTG GCTATATCCT ACGTGTTACA GCGTACAAAG AGGGATATGG AGAAGGTTGC   3120
GTAACGATTC ATGAGATCGA AGACAATACA GACGAACTGA AATTCAGCAA CTGTGTAGAA   3180
GAGGAAGTAT ATCCAAACAA CACGGTAACG TGTAATGATT ATACTGCAAA TCAAGAAGAA   3240
TACGGGGGTG CGTACACTTC TCGTAATCGT GGATATGGTG AATCTTATGA AAGTAATTCT   3300
TCCATACCAG CTGAGTATGC GCCAGTTTAT GAGGAAGCAT ATATAGATGG AAGAAAAGAG   3360
AATCCTTGTG AATCTAACAG AGGATATGGG GATTACACGC CACTACCAGC TGGTTATGTG   3420
ACAAAAGAAT TAGAGTACTT CCCAGAAACC GATAAGGTAT GGATTGAGAT CGGGGAAACG   3480
GAAGGAACAT TCATCGTGGA TAGCGTGGAA TTACTCCTTA TGGAGGAA                3528
```

( 2 ) INFORMATION FOR SEQ ID NO:12:

( i ) SEQUENCE CHARACTERISTICS:
( A ) LENGTH: 1176 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: BACILLUS THURINGIENSIS
( B ) STRAIN: AIZAWAI
( C ) INDIVIDUAL ISOLATE: PS81I ( v i i ) IMMEDIATE SOURCE:
( A ) LIBRARY: LAMBDAGEM (TM) - 11 LIBRARY OF AUGUST SICK
( B ) CLONE: 81IA2

( x i ) SEQUENCE DESCRIPTION: SEQ ID NO:12:

```
Met Asn Asn Gln Asn Gln Cys Val Pro Tyr Asn Cys Leu Asn Asp Pro
1               5                   10                  15
```

-continued

```
Thr Ile Glu Ile Leu Glu Gly Glu Arg Ile Glu Thr Gly Tyr Thr Pro
            20                  25                  30
Ile Asp Ile Ser Leu Ser Leu Thr Gln Phe Leu Leu Ser Glu Phe Val
            35                  40                  45
Pro Gly Ala Gly Phe Val Leu Gly Leu Ile Asp Leu Ile Trp Gly Phe
50                      55                  60
Val Gly Pro Ser Gln Trp Asp Ala Phe Leu Val Gln Ile Glu Gln Leu
65                  70                  75                  80
Ile Asn Gln Arg Ile Glu Glu Phe Ala Arg Asn Gln Ala Ile Ser Arg
                85                  90                  95
Leu Glu Gly Leu Ser Asn Leu Tyr Gln Ile Tyr Ala Glu Ala Phe Arg
            100                 105                 110
Glu Trp Glu Ala Asp Pro Thr Asn Pro Ala Leu Thr Glu Glu Met Arg
            115                 120                 125
Ile Gln Phe Asn Asp Met Asn Ser Ala Leu Thr Thr Ala Ile Pro Leu
130                     135                 140
Phe Thr Val Gln Asn Tyr Gln Val Pro Leu Leu Ser Val Tyr Val Gln
145                 150                 155                 160
Ala Ala Asn Leu His Leu Ser Val Leu Arg Asp Val Ser Val Phe Gly
                165                 170                 175
Gln Arg Trp Gly Phe Asp Val Ala Thr Ile Asn Ser Arg Tyr Asn Asp
            180                 185                 190
Leu Thr Arg Leu Ile Gly Thr Tyr Thr Asp Tyr Ala Val Arg Trp Tyr
            195                 200                 205
Asn Thr Gly Leu Glu Arg Val Trp Gly Pro Asp Ser Arg Asp Trp Val
210                     215                 220
Arg Tyr Asn Gln Phe Arg Arg Glu Leu Thr Leu Thr Val Leu Asp Ile
225                 230                 235                 240
Val Ser Leu Phe Pro Asn Tyr Asp Ser Arg Thr Tyr Pro Ile Arg Thr
                245                 250                 255
Val Ser Gln Leu Thr Arg Glu Ile Tyr Thr Asn Pro Val Leu Glu Asn
            260                 265                 270
Phe Asp Gly Ser Phe Arg Gly Met Ala Gln Arg Ile Glu Gln Asn Ile
            275                 280                 285
Arg Gln Pro His Leu Met Asp Leu Leu Asn Ser Ile Thr Ile Tyr Thr
290                     295                 300
Asp Val His Arg Gly Phe Asn Tyr Trp Ser Gly His Gln Ile Thr Ala
305                 310                 315                 320
Ser Pro Val Gly Phe Ala Gly Pro Glu Phe Thr Phe Pro Arg Tyr Gly
                325                 330                 335
Thr Met Gly Asn Ala Ala Pro Pro Val Leu Ile Ser Thr Thr Gly Leu
            340                 345                 350
Gly Ile Phe Arg Thr Leu Ser Ser Pro Leu Tyr Arg Arg Ile Ile Leu
            355                 360                 365
Gly Ser Gly Pro Asn Asn Gln Asn Leu Phe Val Leu Asp Gly Thr Glu
370                     375                 380
Phe Ser Phe Ala Ser Leu Thr Ala Asp Leu Pro Ser Thr Ile Tyr Arg
385                 390                 395                 400
Gln Arg Gly Thr Val Asp Ser Leu Asp Val Ile Pro Pro Gln Asp Asn
                405                 410                 415
Ser Val Pro Ala Arg Ala Gly Phe Ser His Arg Leu Ser His Val Thr
            420                 425                 430
Met Leu Ser Gln Ala Ala Gly Ala Val Tyr Thr Leu Arg Ala Pro Thr
            435                 440                 445
Phe Ser Trp Arg His Arg Ser Ala Glu Phe Ser Asn Leu Ile Pro Ser
```

|     |     | 450 |     |     |     | 455 |     |     |     | 460 |     |     |     |     |
|-----|-----|-----|-----|-----|-----|-----|-----|-----|-----|-----|-----|-----|-----|-----|

Ser Gln Ile Thr Gln Ile Pro Leu Thr Lys Ser Ile Asn Leu Gly Ser
465                 470                 475                 480

Gly Thr Ser Val Val Lys Gly Pro Gly Phe Thr Gly Gly Asp Ile Leu
                485                 490                 495

Arg Ile Thr Ser Pro Gly Gln Ile Ser Thr Leu Arg Val Thr Ile Thr
            500                 505                 510

Ala Pro Leu Ser Gln Arg Tyr Arg Val Arg Ile Arg Tyr Ala Ser Thr
            515                 520                 525

Thr Asn Leu Gln Phe His Thr Ser Ile Asp Gly Arg Pro Ile Asn Gln
530                 535                 540

Gly Asn Phe Ser Ala Thr Met Ser Ser Gly Gly Asn Leu Gln Ser Gly
545                 550                 555                 560

Ser Phe Arg Thr Ala Gly Phe Thr Thr Pro Phe Asn Phe Ser Asn Gly
                565                 570                 575

Ser Ser Ile Phe Thr Leu Ser Ala His Val Phe Asn Ser Gly Asn Glu
            580                 585                 590

Val Tyr Ile Glu Arg Ile Glu Phe Val Pro Ala Glu Val Thr Phe Glu
            595                 600                 605

Ala Glu Tyr Asp Leu Glu Arg Ala Gln Glu Ala Val Asn Ala Leu Phe
610                 615                 620

Thr Ser Ser Asn Gln Leu Gly Leu Lys Thr Asn Val Thr Asp Tyr His
625                 630                 635                 640

Ile Asp Gln Val Ser Asn Leu Val Glu Cys Leu Ser Gly Glu Phe Cys
                645                 650                 655

Leu Asp Glu Lys Arg Glu Leu Ser Glu Lys Val Lys His Ala Asn Arg
            660                 665                 670

Leu Ser Asp Glu Arg Asn Leu Leu Gln Asp Pro Asn Phe Arg Gly Ile
            675                 680                 685

Asn Arg Gln Pro Asp Arg Gly Trp Arg Gly Ser Thr Asp Ile Thr Ile
690                 695                 700

Gln Gly Gly Asp Asp Val Phe Lys Glu Asn Tyr Val Thr Leu Pro Gly
705                 710                 715                 720

Thr Phe Asn Glu Cys Tyr Pro Thr Tyr Leu Tyr Gln Lys Ile Asp Glu
                725                 730                 735

Ser Lys Leu Lys Ala Tyr Thr Arg Tyr Gln Leu Arg Gly Tyr Ile Glu
            740                 745                 750

Asp Ser Gln His Leu Glu Ile Tyr Leu Ile Arg Tyr Asn Thr Lys His
            755                 760                 765

Glu Thr Val Asn Val Pro Gly Thr Gly Ser Leu Trp Pro Leu Ser Val
770                 775                 780

Glu Asn Pro Ile Gly Lys Cys Gly Glu Pro Asn Arg Cys Ala Pro Gln
785                 790                 795                 800

Leu Glu Trp Asn Pro Asp Leu Asp Cys Ser Cys Arg Asp Gly Glu Lys
                805                 810                 815

Cys Ala His His Ser His His Phe Ser Leu Asp Ile Asp Ile Gly Cys
            820                 825                 830

Thr Asp Leu Asn Glu Asn Leu Gly Val Trp Val Ile Phe Lys Ile Lys
            835                 840                 845

Met Gln Asp Gly His Ala Arg Leu Gly Asn Leu Glu Phe Leu Glu Glu
850                 855                 860

Lys Pro Leu Val Gly Glu Ser Leu Ala Arg Val Lys Arg Ala Glu Lys
865                 870                 875                 880

Lys Trp Arg Asp Lys Arg Glu Lys Leu Gln Val Glu Thr Asn Ile Val
                885                 890                 895

| | | | | | | | | | | | | | | |
|---|---|---|---|---|---|---|---|---|---|---|---|---|---|---|
|Tyr|Lys|Glu|Ala|Lys|Glu|Ser|Val|Asp|Ala|Leu|Phe|Val|Asn|Ser|Gln|
| | | |900| | | |905| | | |910| | | |

Tyr Lys Glu Ala Lys Glu Ser Val Asp Ala Leu Phe Val Asn Ser Gln
                900             905             910

Tyr Asp Arg Leu Gln Ala Asp Thr Asp Ile Ala Met Ile His Ala Ala
            915             920             925

Asp Lys Arg Val His Arg Ile Arg Glu Ala Tyr Leu Pro Glu Leu Ser
        930             935             940

Val Ile Pro Gly Val Asn Ala Gly Ile Phe Glu Glu Leu Glu Gly Arg
945             950             955             960

Ile Phe Thr Ala Tyr Ser Leu Tyr Asp Ala Arg Asn Val Ile Lys Asn
                965             970             975

Gly Asp Phe Asn Asn Gly Leu Ser Cys Trp Asn Val Lys Gly His Val
            980             985             990

Asp Val Glu Glu Gln Asn Asn His Arg Ser Val Leu Val Val Pro Glu
        995             1000            1005

Trp Glu Ala Glu Val Ser Gln Glu Val Arg Val Cys Pro Gly Arg Gly
    1010            1015            1020

Tyr Ile Leu Arg Val Thr Ala Tyr Lys Glu Gly Tyr Gly Glu Gly Cys
1025            1030            1035            1040

Val Thr Ile His Glu Ile Glu Asp Asn Thr Asp Glu Leu Lys Phe Ser
                1045            1050            1055

Asn Cys Val Glu Glu Glu Val Tyr Pro Asn Asn Thr Val Thr Cys Asn
            1060            1065            1070

Asp Tyr Thr Ala Asn Gln Glu Glu Tyr Gly Gly Ala Tyr Thr Ser Arg
        1075            1080            1085

Asn Arg Gly Tyr Gly Glu Ser Tyr Glu Ser Asn Ser Ser Ile Pro Ala
    1090            1095            1100

Glu Tyr Ala Pro Val Tyr Glu Glu Ala Tyr Ile Asp Gly Arg Lys Glu
1105            1110            1115            1120

Asn Pro Cys Glu Ser Asn Arg Gly Tyr Gly Asp Tyr Thr Pro Leu Pro
                1125            1130            1135

Ala Gly Tyr Val Thr Lys Glu Leu Glu Tyr Phe Pro Glu Thr Asp Lys
            1140            1145            1150

Val Trp Ile Glu Ile Gly Glu Thr Glu Gly Thr Phe Ile Val Asp Ser
        1155            1160            1165

Val Glu Leu Leu Leu Met Glu Glu
    1170            1175

( 2 ) INFORMATION FOR SEQ ID NO:13:

( i ) SEQUENCE CHARACTERISTICS:
        ( A ) LENGTH: 3495 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: BACILLUS THURINGIENSIS
        ( B ) STRAIN: AIZAWAI
        ( C ) INDIVIDUAL ISOLATE: PS811

( v i i ) IMMEDIATE SOURCE:
        ( A ) LIBRARY: LAMBDAGEM (TM) - 11 LIBRARY OF AUGUST SICK
        ( B ) CLONE: 811B ( x i ) SEQUENCE DESCRIPTION: SEQ ID NO:13:

ATGGAAATAA ATAATCAAAA CCAATGTGTG CCTTACAATT GTTTAAGTAA TCCTAAGGAG    60

| | | | | | |
|---|---|---|---|---|---|
| ATAATATTAG | GCGAGGAAAG | GCTAGAAACA | GGGAATACTG | TAGCAGACAT | TTCATTAGGG | 120 |
| CTTATTAATT | TTCTATATTC | TAATTTTGTA | CCAGGAGGAG | GATTTATAGT | AGGTTTACTA | 180 |
| GAATTAATAT | GGGGATTTAT | AGGGCCTTCG | CAATGGGATA | TTTTTTTAGC | TCAAATTGAG | 240 |
| CAATTGATTA | GTCAAAGAAT | AGAAGAATTT | GCTAGGAATC | AGGCAATTTC | AAGATTGGAG | 300 |
| GGGCTAAGCA | ATCTTTATAA | GGTCTATGTT | AGAGCGTTTA | GCGACTGGGA | GAAAGATCCT | 360 |
| ACTAATCCTG | CTTTAAGGGA | AGAAATGCGT | ATACAATTTA | ATGACATGAA | TAGTGCTCTC | 420 |
| ATAACGGCTA | TTCCACTTTT | TAGAGTTCAA | AATTATGAAG | TTGCTCTTTT | ATCTGTATAT | 480 |
| GTTCAAGCCG | CAAACTTACA | TTTATCTATT | TTAAGGGATG | TTTCAGTTTT | CGGAGAAAGA | 540 |
| TGGGGATATG | ATACAGCGAC | TATCAATAAT | CGCTATAGTG | ATCTGACTAG | CCTTATTCAT | 600 |
| GTTTATACTA | ACCATTGTGT | GGATACGTAT | AATCAGGGAT | TAAGGCGTTT | GGAAGGTCGT | 660 |
| TTTCTTAGCG | ATTGGATTGT | ATATAATCGT | TTCCGGAGAC | AATTGACAAT | TTCAGTATTA | 720 |
| GATATTGTTG | CGTTTTTTCC | AAATTATGAT | ATTAGAACAT | ATCCAATTCA | AACAGCTACT | 780 |
| CAGCTAACGA | GGGAAGTCTA | TCTGGATTTA | CCTTTTATTA | ATGAAAATCT | TTCTCCTGCA | 840 |
| GCAAGCTATC | CAACCTTTTC | AGCTGCTGAA | AGTGCTATAA | TTAGAAGTCC | TCATTTAGTA | 900 |
| GACTTTTTAA | ATAGCTTTAC | CATTTATACA | GATAGTCTGG | CACGTTATGC | ATATTGGGGA | 960 |
| GGGCACTTGG | TAAATTCTTT | CCGCACAGGA | ACCACTACTA | ATTTGATAAG | ATCCCCTTTA | 1020 |
| TATGGAAGGG | AAGGAAATAC | AGAGCGCCCC | GTAACTATTA | CCGCATCACC | TAGCGTACCA | 1080 |
| ATATTTAGAA | CACTTTCATA | TATTACAGGC | CTTGACAATT | CAAATCCTGT | AGCTGGAATC | 1140 |
| GAGGGAGTGG | AATTCCAAAA | TACTATAAGT | AGAAGTATCT | ATCGTAAAAG | CGGTCCAATA | 1200 |
| GATTCTTTTA | GTGAATTACC | ACCTCAAGAT | GCCAGCGTAT | CTCCTGCAAT | TGGGTATAGT | 1260 |
| CACCGTTTAT | GCCATGCAAC | ATTTTTAGAA | CGGATTAGTG | ACCAAGAAT | AGCAGGCACC | 1320 |
| GTATTTTCTT | GGACACACCG | TAGTGCCAGC | CCTACTAATG | AAGTAAGTCC | ATCTAGAATT | 1380 |
| ACACAAATTC | CATGGGTAAA | GGCGCATACT | CTTGCATCTG | GTGCCTCCGT | CATTAAAGGT | 1440 |
| CCTGGATTTA | CAGGTGGAGA | TATTCTGACT | AGGAATAGTA | TGGGCGAGCT | GGGGACCTTA | 1500 |
| CGAGTAACCT | TCACAGGAAG | ATTACCACAA | AGTTATTATA | TACGTTTCCG | TTATGCTTCG | 1560 |
| GTAGCAAATA | GGAGTGGTAC | ATTTAGATAT | TCACAGCCAC | CTTCGTATGG | AATTTCATTT | 1620 |
| CCAAAAACTA | TGGACGCAGG | TGAACCACTA | ACATCTCGTT | CGTTCGCTCA | TACAACACTC | 1680 |
| TTCACTCCAA | TAACCTTTTC | ACGAGCTCAA | GAAGAATTTG | ATCTATACAT | CCAATCGGGT | 1740 |
| GTTTATATAG | ATCGAATTGA | ATTTATACCG | GTTACTGCAA | CATTTGAGGC | AGAATATGAT | 1800 |
| TTAGAAAGAG | CGCAAAAGGT | GGTGAATGCC | CTGTTTACGT | CTACAAACCA | ACTAGGGCTA | 1860 |
| AAAACAGATG | TGACGGATTA | TCATATTGAT | CAGGTATCCA | ATCTAGTTGC | GTGTTTATCG | 1920 |
| GATGAATTTT | GTCTGGATGA | AAAGAGAGAA | TTGTCCGAGA | AAGTTAAACA | TGCAAAGCGA | 1980 |
| CTCAGTGATG | AGCGGAATTT | ACTTCAAGAT | CCAAACTTCA | GAGGGATCAA | TAGGCAACCA | 2040 |
| GACCGTGGCT | GGAGAGGAAG | TACGGATATT | ACTATCCAAG | GAGGAGATGA | CGTATTCAAA | 2100 |
| GAGAATTACG | TTACGCTACC | GGGTACCTTT | GATGAGTGCT | ATCCAACGTA | TTTATATCAA | 2160 |
| AAAATAGATG | AGTCGAAATT | AAAAGCCTAT | ACCCGTTATC | AATTAAGAGG | GTATATCGAA | 2220 |
| GATAGTCAAG | ACTTAGAAAT | CTATTTAATT | CGTTACAATG | CAAAACACGA | AATAGTAAAT | 2280 |
| GTACCAGGTA | CAGGAAGTTT | ATGGCCTCTT | TCTGTAGAAA | ATCAAATTGG | ACCTTGTGGA | 2340 |
| GAACCGAATC | GATGCGCGCC | ACACCTTGAA | TGGAATCCTG | ATTTACACTG | TTCCTGCAGA | 2400 |
| GACGGGGAAA | AATGTGCACA | TCATTCTCAT | CATTTCTCTT | TGGACATTGA | TGTTGGATGT | 2460 |
| ACAGACTTAA | ATGAGGACTT | AGGTGTATGG | GTGATATTCA | AGATTAAGAC | GCAAGATGGC | 2520 |

| | | | | | | |
|---|---|---|---|---|---|---|
| CACGCACGAC | TAGGGAATCT | AGAGTTTCTC | GAAGAGAAAC | CATTATTAGG | AGAAGCACTA | 2580 |
| GCTCGTGTGA | AAAGAGCGGA | GAAAAATGG | AGAGACAAAC | GCGAAACATT | ACAATTGGAA | 2640 |
| ACAACTATCG | TTTATAAAGA | GGCAAAGAA | TCTGTAGATG | CTTTATTTGT | AAACTCTCAA | 2700 |
| TATGATAGAT | TACAAGCGGA | TACGAACATC | GCGATGATTC | ATGCGGCAGA | TAAACGCGTT | 2760 |
| CATAGAATTC | GAGAAGCGTA | TCTGCCGGAG | CTGTCTGTGA | TTCCGGGTGT | CAATGCGGCT | 2820 |
| ATTTTTGAAG | AATTAGAAGA | GCGTATTTTC | ACTGCATTTT | CCCTATATGA | TGCGAGAAAT | 2880 |
| ATTATTAAAA | ATGGCGATTT | CAATAATGGC | TTATTATGCT | GGAACGTGAA | AGGGCATGTA | 2940 |
| GAGGTAGAAG | AACAAAACAA | TCACCGTTCA | GTCCTGGTTA | TCCCAGAATG | GGAGGCAGAA | 3000 |
| GTGTCACAAG | AGGTTCGTGT | CTGTCCAGGT | CGTGGCTATA | TCCTTCGTGT | TACAGCGTAC | 3060 |
| AAAGAGGGAT | ATGGAGAAGG | TTGCGTAACG | ATCCATGAGA | TCGAGAACAA | TACAGACGAA | 3120 |
| CTGAAATTCA | ACAACTGTGT | AGAAGAGGAA | GTATATCCAA | ACAACACGGT | AACGTGTATT | 3180 |
| AATTATACTG | CGACTCAAGA | AGAATATGAG | GGTACGTACA | CTTCTCGTAA | TCGAGGATAT | 3240 |
| GACGAAGCCT | ATGGTAATAA | CCCTTCCGTA | CCAGCTGATT | ATGCGTCAGT | CTATGAAGAA | 3300 |
| AAATCGTATA | CAGATAGACG | AAGAGAGAAT | CCTTGTGAAT | CTAACAGAGG | ATATGGAGAT | 3360 |
| TACACACCAC | TACCAGCTGG | TTATGTAACA | AAGGAATTAG | AGTACTTCCC | AGAGACCGAT | 3420 |
| AAGGTATGGA | TTGAGATTGG | AGAAACAGAA | GGAACATTCA | TCGTGGACAG | CGTGGAATTA | 3480 |
| CTCCTTATGG | AGGAA | | | | | 3495 |

(2) INFORMATION FOR SEQ ID NO:14:

(i) SEQUENCE CHARACTERISTICS:
        (A) LENGTH: 1165 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: NO (vi) ORIGINAL SOURCE:
        (A) ORGANISM: BACILLUS THURINGIENSIS
        (B) STRAIN: AIZAWAI
        (C) INDIVIDUAL ISOLATE: PS81I (vii) IMMEDIATE SOURCE:
        (A) LIBRARY: LAMBDAGEM (TM) - 11 LIBRARY OF AUGUST SICK
        (B) CLONE: 81IB (xi) SEQUENCE DESCRIPTION: SEQ ID NO:14:

```
Met Glu Ile Asn Asn Gln Asn Gln Cys Val Pro Tyr Asn Cys Leu Ser
 1               5                  10                  15

Asn Pro Lys Glu Ile Ile Leu Gly Glu Glu Arg Leu Glu Thr Gly Asn
            20                  25                  30

Thr Val Ala Asp Ile Ser Leu Gly Leu Ile Asn Phe Leu Tyr Ser Asn
        35                  40                  45

Phe Val Pro Gly Gly Gly Phe Ile Val Gly Leu Leu Glu Leu Ile Trp
    50                  55                  60

Gly Phe Ile Gly Pro Ser Gln Trp Asp Ile Phe Leu Ala Gln Ile Glu
65                  70                  75                  80

Gln Leu Ile Ser Gln Arg Ile Glu Glu Phe Ala Arg Asn Gln Ala Ile
                85                  90                  95

Ser Arg Leu Glu Gly Leu Ser Asn Leu Tyr Lys Val Tyr Val Arg Ala
            100                 105                 110
```

```
Phe Ser Asp Trp Glu Lys Asp Pro Thr Asn Pro Ala Leu Arg Glu Glu
        115                 120                 125

Met Arg Ile Gln Phe Asn Asp Met Asn Ser Ala Leu Ile Thr Ala Ile
    130                 135                 140

Pro Leu Phe Arg Val Gln Asn Tyr Glu Val Ala Leu Leu Ser Val Tyr
145                 150                 155                 160

Val Gln Ala Ala Asn Leu His Leu Ser Ile Leu Arg Asp Val Ser Val
                165                 170                 175

Phe Gly Glu Arg Trp Gly Tyr Asp Thr Ala Thr Ile Asn Asn Arg Tyr
            180                 185                 190

Ser Asp Leu Thr Ser Leu Ile His Val Tyr Thr Asn His Cys Val Asp
        195                 200                 205

Thr Tyr Asn Gln Gly Leu Arg Arg Leu Glu Gly Arg Phe Leu Ser Asp
    210                 215                 220

Trp Ile Val Tyr Asn Arg Phe Arg Arg Gln Leu Thr Ile Ser Val Leu
225                 230                 235                 240

Asp Ile Val Ala Phe Phe Pro Asn Tyr Asp Ile Arg Thr Tyr Pro Ile
                245                 250                 255

Gln Thr Ala Thr Gln Leu Thr Arg Glu Val Tyr Leu Asp Leu Pro Phe
            260                 265                 270

Ile Asn Glu Asn Leu Ser Pro Ala Ala Ser Tyr Pro Thr Phe Ser Ala
        275                 280                 285

Ala Glu Ser Ala Ile Ile Arg Ser Pro His Leu Val Asp Phe Leu Asn
    290                 295                 300

Ser Phe Thr Ile Tyr Thr Asp Ser Leu Ala Arg Tyr Ala Tyr Trp Gly
305                 310                 315                 320

Gly His Leu Val Asn Ser Phe Arg Thr Gly Thr Thr Thr Asn Leu Ile
                325                 330                 335

Arg Ser Pro Leu Tyr Gly Arg Glu Gly Asn Thr Glu Arg Pro Val Thr
            340                 345                 350

Ile Thr Ala Ser Pro Ser Val Pro Ile Phe Arg Thr Leu Ser Tyr Ile
        355                 360                 365

Thr Gly Leu Asp Asn Ser Asn Pro Val Ala Gly Ile Glu Gly Val Glu
    370                 375                 380

Phe Gln Asn Thr Ile Ser Arg Ser Ile Tyr Arg Lys Ser Gly Pro Ile
385                 390                 395                 400

Asp Ser Phe Ser Glu Leu Pro Pro Gln Asp Ala Ser Val Ser Pro Ala
                405                 410                 415

Ile Gly Tyr Ser His Arg Leu Cys His Ala Thr Phe Leu Glu Arg Ile
            420                 425                 430

Ser Gly Pro Arg Ile Ala Gly Thr Val Phe Ser Trp Thr His Arg Ser
        435                 440                 445

Ala Ser Pro Thr Asn Glu Val Ser Pro Ser Arg Ile Thr Gln Ile Pro
    450                 455                 460

Trp Val Lys Ala His Thr Leu Ala Ser Gly Ala Ser Val Ile Lys Gly
465                 470                 475                 480

Pro Gly Phe Thr Gly Gly Asp Ile Leu Thr Arg Asn Ser Met Gly Glu
                485                 490                 495

Leu Gly Thr Leu Arg Val Thr Phe Thr Gly Arg Leu Pro Gln Ser Tyr
            500                 505                 510

Tyr Ile Arg Phe Arg Tyr Ala Ser Val Ala Asn Arg Ser Gly Thr Phe
        515                 520                 525

Arg Tyr Ser Gln Pro Pro Ser Tyr Gly Ile Ser Phe Pro Lys Thr Met
    530                 535                 540

Asp Ala Gly Glu Pro Leu Thr Ser Arg Ser Phe Ala His Thr Thr Leu
```

```
545                 550                 555                 560

Phe Thr Pro Ile Thr Phe Ser Arg Ala Gln Glu Phe Asp Leu Tyr
                565             570             575

Ile Gln Ser Gly Val Tyr Ile Asp Arg Ile Glu Phe Ile Pro Val Thr
            580             585             590

Ala Thr Phe Glu Ala Glu Tyr Asp Leu Glu Arg Ala Gln Lys Val Val
        595             600             605

Asn Ala Leu Phe Thr Ser Thr Asn Gln Leu Gly Leu Lys Thr Asp Val
610             615             620

Thr Asp Tyr His Ile Asp Gln Val Ser Asn Leu Val Ala Cys Leu Ser
625             630             635             640

Asp Glu Phe Cys Leu Asp Glu Lys Arg Glu Leu Ser Glu Lys Val Lys
                645             650             655

His Ala Lys Arg Leu Ser Asp Glu Arg Asn Leu Leu Gln Asp Pro Asn
            660             665             670

Phe Arg Gly Ile Asn Arg Gln Pro Asp Arg Gly Trp Arg Gly Ser Thr
        675             680             685

Asp Ile Thr Ile Gln Gly Gly Asp Asp Val Phe Lys Glu Asn Tyr Val
    690             695             700

Thr Leu Pro Gly Thr Phe Asp Glu Cys Tyr Pro Thr Tyr Leu Tyr Gln
705             710             715             720

Lys Ile Asp Glu Ser Lys Leu Lys Ala Tyr Thr Arg Tyr Gln Leu Arg
                725             730             735

Gly Tyr Ile Glu Asp Ser Gln Asp Leu Glu Ile Tyr Leu Ile Arg Tyr
            740             745             750

Asn Ala Lys His Glu Ile Val Asn Val Pro Gly Thr Gly Ser Leu Trp
        755             760             765

Pro Leu Ser Val Glu Asn Gln Ile Gly Pro Cys Gly Glu Pro Asn Arg
770             775             780

Cys Ala Pro His Leu Glu Trp Asn Pro Asp Leu His Cys Ser Cys Arg
785             790             795             800

Asp Gly Glu Lys Cys Ala His His Ser His His Phe Ser Leu Asp Ile
                805             810             815

Asp Val Gly Cys Thr Asp Leu Asn Glu Asp Leu Gly Val Trp Val Ile
            820             825             830

Phe Lys Ile Lys Thr Gln Asp Gly His Ala Arg Leu Gly Asn Leu Glu
        835             840             845

Phe Leu Glu Glu Lys Pro Leu Gly Glu Ala Leu Ala Arg Val Lys
850             855             860

Arg Ala Glu Lys Lys Trp Arg Asp Lys Arg Glu Thr Leu Gln Leu Glu
865             870             875             880

Thr Thr Ile Val Tyr Lys Glu Ala Lys Glu Ser Val Asp Ala Leu Phe
                885             890             895

Val Asn Ser Gln Tyr Asp Arg Leu Gln Ala Asp Thr Asn Ile Ala Met
            900             905             910

Ile His Ala Ala Asp Lys Arg Val His Arg Ile Arg Glu Ala Tyr Leu
        915             920             925

Pro Glu Leu Ser Val Ile Pro Gly Val Asn Ala Ala Ile Phe Glu Glu
    930             935             940

Leu Glu Glu Arg Ile Phe Thr Ala Phe Ser Leu Tyr Asp Ala Arg Asn
945             950             955             960

Ile Ile Lys Asn Gly Asp Phe Asn Asn Gly Leu Leu Cys Trp Asn Val
                965             970             975

Lys Gly His Val Glu Val Glu Glu Gln Asn Asn His Arg Ser Val Leu
            980             985             990
```

| | | | | | | | | | | | | |
|---|---|---|---|---|---|---|---|---|---|---|---|---|
|Val|Ile|Pro|Glu|Trp|Glu|Ala|Glu|Val|Ser|Gln|Glu|Val|Arg|Val|Cys|
| | |995| | |1000| | | | |1005| | |

Val Ile Pro Glu Trp Glu Ala Glu Val Ser Gln Glu Val Arg Val Cys
            995             1000                1005

Pro Gly Arg Gly Tyr Ile Leu Arg Val Thr Ala Tyr Lys Glu Gly Tyr
        1010            1015            1020

Gly Glu Gly Cys Val Thr Ile His Glu Ile Glu Asn Asn Thr Asp Glu
1025                1030            1035                1040

Leu Lys Phe Asn Asn Cys Val Glu Glu Val Tyr Pro Asn Asn Thr
            1045                1050                1055

Val Thr Cys Ile Asn Tyr Thr Ala Thr Gln Glu Glu Tyr Glu Gly Thr
            1060                1065            1070

Tyr Thr Ser Arg Asn Arg Gly Tyr Asp Glu Ala Tyr Gly Asn Asn Pro
        1075                1080            1085

Ser Val Pro Ala Asp Tyr Ala Ser Val Tyr Glu Glu Lys Ser Tyr Thr
    1090                1095                1100

Asp Arg Arg Arg Glu Asn Pro Cys Glu Ser Asn Arg Gly Tyr Gly Asp
1105                1110            1115                1120

Tyr Thr Pro Leu Pro Ala Gly Tyr Val Thr Lys Glu Leu Glu Tyr Phe
                1125            1130                1135

Pro Glu Thr Asp Lys Val Trp Ile Glu Ile Gly Glu Thr Glu Gly Thr
            1140                1145            1150

Phe Ile Val Asp Ser Val Glu Leu Leu Leu Met Glu Glu
            1155            1160            1165

(2) INFORMATION FOR SEQ ID NO:15:

(i) SEQUENCE CHARACTERISTICS:
        (A) LENGTH: 3567 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: BACILLUS THURINGIENSIS
        (B) STRAIN: AIZAWAI
        (C) INDIVIDUAL ISOLATE: PS811

&nb

-continued

| | | | | | |
|---|---|---|---|---|---|
| ACGTATCAAG | ATTGGATAAC | ATATAATCGA | TTACGGAGAG | ACTTAACATT | GACTGTATTA | 720
| GATATCGCCG | CTTTCTTTCC | AAACTATGAC | AATAGGAGAT | ATCCAATTCA | GCCAGTTGGT | 780
| CAACTAACAA | GGGAAGTTTA | TACGGACCCA | TTAATTAATT | TTAATCCACA | GTTACAGTCT | 840
| GTAGCTCAAT | TACCTACTTT | TAACGTTATG | GAGAGCAGCG | CAATTAGAAA | TCCTCATTTA | 900
| TTTGATATAT | TGAATAATCT | TACAATCTTT | ACGGATTGGT | TTAGTGTTGG | ACGCAATTTT | 960
| TATTGGGGAG | GACATCGAGT | AATATCTAGC | CTTATAGGAG | GTGGTAACAT | AACATCTCCT | 1020
| ATATATGGAA | GAGAGGCGAA | CCAGGAGCCT | CCAAGATCCT | TTACTTTTAA | TGGACCGGTA | 1080
| TTTAGGACTT | TATCAAATCC | TACTTTACGA | TTATTACAGC | AACCTTGGCC | AGCGCCACCA | 1140
| TTTAATTTAC | GTGGTGTTGA | AGGAGTAGAA | TTTTCTACAC | CTACAAATAG | CTTTACGTAT | 1200
| CGAGGAAGAG | GTCAGGTTGA | TTCTTTAACT | GAATTACCGC | CTGAGGATAA | TAGTGTGCCA | 1260
| CCTCGCGAAG | GATATAGTCA | TCGTTTATGT | CATGCAACTT | TTGTTCAAAG | ATCTGGAACA | 1320
| CCTTTTTTAA | CAACTGGTGT | AGTATTTTCT | TGGACGCATC | GTAGTGCAAC | TCTTACAAAT | 1380
| ACAATTGATC | CAGAGAGAAT | TAATCAAATA | CCTTTAGTGA | AAGGATTTAG | AGTTTGGGGG | 1440
| GGCACCTCTG | TCATTACAGG | ACCAGGATTT | ACAGGAGGGG | ATATCCTTCG | AAGAAATACC | 1500
| TTTGGTGATT | TTGTATCTCT | ACAAGTCAAT | ATTAATTCAC | CAATTACCCA | AAGATACCGT | 1560
| TTAAGATTTC | GTTACGCTTC | CAGTAGGGAT | GCACGAGTTA | TAGTATTAAC | AGGAGCGGCA | 1620
| TCCACAGGAG | TGGGAGGCCA | AGTTAGTGTA | AATATGCCTC | TTCAGAAAAC | TATGGAAATA | 1680
| GGGGAGAACT | TAACATCTAG | AACATTTAGA | TATACCGATT | TTAGTAATCC | TTTTTCATTT | 1740
| AGAGCTAATC | CAGATATAAT | TGGGATAAGT | GAACAACCTC | TATTTGGTGC | AGGTTCTATT | 1800
| AGTAGCGGTG | AACTTTATAT | AGATAAAATT | GAAATTATTC | TAGCAGATGC | AACATTTGAA | 1860
| GCAGAATCTG | ATTTAGAAAG | AGCACAAAAG | GCGGTGAATG | CCCTGTTTAC | TTCTTCCAAT | 1920
| CAAATCGGGT | TAAAACCGA | TGTGACGGAT | TATCATATTG | ATCAAGTATC | CAATTTAGTG | 1980
| GATTGTTTAT | CAGATGAATT | TTGTCTGGAT | GAAAAGCGAG | AATTGTCCGA | GAAAGTCAAA | 2040
| CATGCGAAGC | GACTCAGTGA | TGAGCGGAAT | TTACTTCAAG | ATCCAAACTT | CAGAGGGATC | 2100
| AATAGACAAC | CAGACCGTGG | CTGGAGAGGA | AGTACAGATA | TTACCATCCA | AGGAGGAGAT | 2160
| GACGTATTCA | AAGAGAATTA | CGTCACACTA | CCGGGTACCG | TTGATGAGTG | CTATCCAACG | 2220
| TATTTATATC | AGAAAATAGA | TGAGTCGAAA | TTAAAAGCTT | ATACCCGTTA | TGAATTAAGA | 2280
| GGGTATATCG | AAGATAGTCA | AGACTTAGAA | ATCTATTTGA | TCCGTTACAA | TGCAAAACAC | 2340
| GAAATAGTAA | ATGTGCCAGG | CACGGGTTCC | TTATGGCCGC | TTTCAGCCCA | AAGTCCAATC | 2400
| GGAAAGTGTG | GAGAACCGAA | TCGATGCGCG | CCACACCTTG | AATGGAATCC | TGATCTAGAT | 2460
| TGTTCCTGCA | GAGACGGGGA | AAAATGTGCA | CATCATTCCC | ATCATTTCAC | CTTGGATATT | 2520
| GATGTTGGAT | GTACAGACTT | AAATGAGGAC | TTAGGTCTAT | GGGTGATATT | CAAGATTAAG | 2580
| ACGCAAGATA | ACCATGCAAG | ACTAGGGAAT | CTAGAGTTTC | TCGAAGAGAA | ACCATTATTA | 2640
| GGGGAAGCAC | TAGCTCGTGT | GAAAAGAGCG | GAGAAGAAGT | GGAGAGACAA | ACGAGAGAAA | 2700
| CTGCAGTTGG | AAACAAATAT | TGTTTATAAA | GAGGCAAAAG | AATCTGTAGA | TGCTTTATTT | 2760
| GTAAACTCTC | AATATGATAG | ATTACAAGTG | AATACGAACA | TCGCAATGAT | TCATGCGGCA | 2820
| GATAAACGCG | TTCATAGAAT | CCGGGAAGCG | TATCTGCCAG | AGTTGTCTGT | GATTCCAGGT | 2880
| GTCAATGCGG | CCATTTTCGA | AGAATTAGAG | GGACGTATTT | TTACAGCGTA | TTCCTTATAT | 2940
| GATGCGAGAA | ATGTCATTAA | AAATGGCGAT | TTCAATAATG | GCTTATTATG | CTGGAACGTG | 3000
| AAAGGTCATG | TAGATGTAGA | AGAGCAAAAC | AACCACCGTT | CGGTCCTTGT | TATCCCAGAA | 3060
| TGGGAGGCAG | AAGTGTCACA | AGAGGTTCGT | GTCTGTCCAG | GTCGTGGCTA | TATCCTTCGT | 3120

-continued

```
GTCACAGCAT ATAAAGAGGG ATATGGAGAG GGCTGCGTAA CGATCCATGA GATCGAAGAC    3180

AATACAGACG AACTGAAATT CAGCAACTGT GTAGAAGAGG AAGTATATCC AAACAACACA    3240

GTAACGTGTA ATAATTATAC TGGGACTCAA GAAGAATATG AGGGTACGTA CACTTCTCGT    3300

AATCAAGGAT ATGACGAAGC CTATGGTAAT AACCCTTCCG TACCAGCTGA TTACGCTTCA    3360

GTCTATGAAG AAAAATCGTA TACAGATGGA CGAAGAGAGA ATCCTTGTGA ATCTAACAGA    3420

GGCTATGGGG ATTACACACC ACTACCGGCT GGTTATGTAA CAAAGGATTT AGAGTACTTC    3480

CCAGAGACCG ATAAGGTATG GATTGAGATC GGAGAAACAG AAGGAACATT CATCGTGGAT    3540

AGCGTGGAAT TACTCCTTAT GGAGGAA                                         3567
```

( 2 ) INFORMATION FOR SEQ ID NO:16:

( i ) SEQUENCE CHARACTERISTICS:
        ( A ) LENGTH: 1189 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
        ( A ) ORGANISM: BACILLUS THURINGIENSIS
        ( B ) STRAIN: AIZAWAI
        ( C ) INDIVIDUAL ISOLATE: PS81I ( v i i ) IMMEDIATE SOURCE:
        ( A ) LIBRARY: LAMBDAGEM (TM) - 11 LIBRARY OF AUGUST SICK
        ( B ) CLONE: 81IB2

( x i ) SEQUENCE DESCRIPTION: SEQ ID NO:16:

```
Met Glu Glu Asn Asn Gln Asn Gln Cys Ile Pro Tyr Asn Cys Leu Ser
 1               5                  10                  15

Asn Pro Glu Glu Val Leu Leu Asp Gly Glu Arg Ile Ser Thr Gly Asn
             20                  25                  30

Ser Ser Ile Asp Ile Ser Leu Ser Leu Val Gln Phe Leu Val Ser Asn
         35                  40                  45

Phe Val Pro Gly Gly Gly Phe Leu Val Gly Leu Ile Asp Phe Val Trp
     50                  55                  60

Gly Ile Val Gly Pro Ser Gln Trp Asp Ala Phe Leu Val Gln Ile Glu
 65                  70                  75                  80

Gln Leu Ile Asn Glu Arg Ile Ala Glu Phe Ala Arg Asn Ala Ala Ile
                 85                  90                  95

Ala Asn Leu Glu Gly Leu Gly Asn Asn Phe Asn Ile Tyr Val Glu Ala
            100                 105                 110

Phe Lys Glu Trp Glu Glu Asp Pro Asn Asn Pro Ala Thr Arg Thr Arg
        115                 120                 125

Val Ile Asp Arg Phe Arg Ile Leu Asp Gly Leu Leu Glu Arg Asp Ile
    130                 135                 140

Pro Ser Phe Arg Ile Ser Gly Phe Glu Val Pro Leu Leu Ser Val Tyr
145                 150                 155                 160

Ala Gln Ala Ala Asn Leu His Leu Ala Ile Leu Arg Asp Ser Val Ile
                165                 170                 175

Phe Gly Glu Arg Trp Gly Leu Thr Thr Ile Asn Val Asn Glu Asn Tyr
            180                 185                 190

Asn Arg Leu Ile Arg His Ile Asp Glu Tyr Ala Asp His Cys Ala Asn
        195                 200                 205

Thr Tyr Asn Arg Gly Leu Asn Asn Leu Pro Lys Ser Thr Tyr Gln Asp
```

-continued

```
            210                    215                       220
Trp Ile Thr Tyr Asn Arg Leu Arg Arg Asp Leu Thr Leu Thr Val Leu
225                     230                 235                 240
Asp Ile Ala Ala Phe Pro Asn Tyr Asp Asn Arg Arg Tyr Pro Ile
                245                 250                 255
Gln Pro Val Gly Gln Leu Thr Arg Glu Val Tyr Thr Asp Pro Leu Ile
            260                     265                 270
Asn Phe Asn Pro Gln Leu Gln Ser Val Ala Gln Leu Pro Thr Phe Asn
        275                     280                 285
Val Met Glu Ser Ser Ala Ile Arg Asn Pro His Leu Phe Asp Ile Leu
290                     295                 300
Asn Asn Leu Thr Ile Phe Thr Asp Trp Phe Ser Val Gly Arg Asn Phe
305                     310                 315                 320
Tyr Trp Gly Gly His Arg Val Ile Ser Ser Leu Ile Gly Gly Asn
                325                 330                 335
Ile Thr Ser Pro Ile Tyr Gly Arg Glu Ala Asn Gln Glu Pro Pro Arg
                340                 345                 350
Ser Phe Thr Phe Asn Gly Pro Val Phe Arg Thr Leu Ser Asn Pro Thr
            355                 360                 365
Leu Arg Leu Leu Gln Gln Pro Trp Pro Ala Pro Pro Phe Asn Leu Arg
370                     375                 380
Gly Val Glu Gly Val Glu Phe Ser Thr Pro Thr Asn Ser Phe Thr Tyr
385                     390                 395                 400
Arg Gly Arg Gly Gln Val Asp Ser Leu Thr Glu Leu Pro Pro Glu Asp
                405                 410                 415
Asn Ser Val Pro Pro Arg Glu Gly Tyr Ser His Arg Leu Cys His Ala
                420                 425                 430
Thr Phe Val Gln Arg Ser Gly Thr Pro Phe Leu Thr Thr Gly Val Val
            435                 440                 445
Phe Ser Trp Thr His Arg Ser Ala Thr Leu Thr Asn Thr Ile Asp Pro
450                     455                 460
Glu Arg Ile Asn Gln Ile Pro Leu Val Lys Gly Phe Arg Val Trp Gly
465                     470                 475                 480
Gly Thr Ser Val Ile Thr Gly Pro Gly Phe Thr Gly Gly Asp Ile Leu
                485                 490                 495
Arg Arg Asn Thr Phe Gly Asp Phe Val Ser Leu Gln Val Asn Ile Asn
                500                 505                 510
Ser Pro Ile Thr Gln Arg Tyr Arg Leu Arg Phe Arg Tyr Ala Ser Ser
            515                 520                 525
Arg Asp Ala Arg Val Ile Val Leu Thr Gly Ala Ala Ser Thr Gly Val
530                     535                 540
Gly Gly Gln Val Ser Val Asn Met Pro Leu Gln Lys Thr Met Glu Ile
545                     550                 555                 560
Gly Glu Asn Leu Thr Ser Arg Thr Phe Arg Tyr Thr Asp Phe Ser Asn
                565                 570                 575
Pro Phe Ser Phe Arg Ala Asn Pro Asp Ile Ile Gly Ile Ser Glu Gln
                580                 585                 590
Pro Leu Phe Gly Ala Gly Ser Ile Ser Ser Gly Glu Leu Tyr Ile Asp
            595                 600                 605
Lys Ile Glu Ile Ile Leu Ala Asp Ala Thr Phe Glu Ala Glu Ser Asp
610                     615                 620
Leu Glu Arg Ala Gln Lys Ala Val Asn Ala Leu Phe Thr Ser Ser Asn
625                     630                 635                 640
Gln Ile Gly Leu Lys Thr Asp Val Thr Asp Tyr His Ile Asp Gln Val
                645                 650                 655
```

```
Ser Asn Leu Val Asp Cys Leu Ser Asp Glu Phe Cys Leu Asp Glu Lys
            660             665             670
Arg Glu Leu Ser Glu Lys Val Lys His Ala Lys Arg Leu Ser Asp Glu
            675             680             685
Arg Asn Leu Leu Gln Asp Pro Asn Phe Arg Gly Ile Asn Arg Gln Pro
            690             695             700
Asp Arg Gly Trp Arg Gly Ser Thr Asp Ile Thr Ile Gln Gly Gly Asp
705             710             715             720
Asp Val Phe Lys Glu Asn Tyr Val Thr Leu Pro Gly Thr Val Asp Glu
            725             730             735
Cys Tyr Pro Thr Tyr Leu Tyr Gln Lys Ile Asp Glu Ser Lys Leu Lys
            740             745             750
Ala Tyr Thr Arg Tyr Glu Leu Arg Gly Tyr Ile Glu Asp Ser Gln Asp
            755             760             765
Leu Glu Ile Tyr Leu Ile Arg Tyr Asn Ala Lys His Glu Ile Val Asn
            770             775             780
Val Pro Gly Thr Gly Ser Leu Trp Pro Leu Ser Ala Gln Ser Pro Ile
785             790             795             800
Gly Lys Cys Gly Glu Pro Asn Arg Cys Ala Pro His Leu Glu Trp Asn
                805             810             815
Pro Asp Leu Asp Cys Ser Cys Arg Asp Gly Glu Lys Cys Ala His His
            820             825             830
Ser His His Phe Thr Leu Asp Ile Asp Val Gly Cys Thr Asp Leu Asn
            835             840             845
Glu Asp Leu Gly Leu Trp Val Ile Phe Lys Ile Lys Thr Gln Asp Asn
850             855             860
His Ala Arg Leu Gly Asn Leu Glu Phe Leu Glu Glu Lys Pro Leu Leu
865             870             875             880
Gly Glu Ala Leu Ala Arg Val Lys Arg Ala Glu Lys Lys Trp Arg Asp
                885             890             895
Lys Arg Glu Lys Leu Gln Leu Glu Thr Asn Ile Val Tyr Lys Glu Ala
            900             905             910
Lys Glu Ser Val Asp Ala Leu Phe Val Asn Ser Gln Tyr Asp Arg Leu
            915             920             925
Gln Val Asn Thr Asn Ile Ala Met Ile His Ala Ala Asp Lys Arg Val
            930             935             940
His Arg Ile Arg Glu Ala Tyr Leu Pro Glu Leu Ser Val Ile Pro Gly
945             950             955             960
Val Asn Ala Ala Ile Phe Glu Glu Leu Glu Gly Arg Ile Phe Thr Ala
                965             970             975
Tyr Ser Leu Tyr Asp Ala Arg Asn Val Ile Lys Asn Gly Asp Phe Asn
            980             985             990
Asn Gly Leu Leu Cys Trp Asn Val Lys Gly His Val Asp Val Glu Glu
            995             1000            1005
Gln Asn Asn His Arg Ser Val Leu Val Ile Pro Glu Trp Glu Ala Glu
            1010            1015            1020
Val Ser Gln Glu Val Arg Val Cys Pro Gly Arg Gly Tyr Ile Leu Arg
1025            1030            1035            1040
Val Thr Ala Tyr Lys Glu Gly Tyr Gly Glu Gly Cys Val Thr Ile His
                1045            1050            1055
Glu Ile Glu Asp Asn Thr Asp Glu Leu Lys Phe Ser Asn Cys Val Glu
            1060            1065            1070
Glu Glu Val Tyr Pro Asn Asn Thr Val Thr Cys Asn Asn Tyr Thr Gly
            1075            1080            1085
```

```
Thr Gln Glu Glu Tyr Glu Gly Thr Tyr Thr Ser Arg Asn Gln Gly Tyr
    1090            1095                1100

Asp Glu Ala Tyr Gly Asn Asn Pro Ser Val Pro Ala Asp Tyr Ala Ser
1105                1110            1115                1120

Val Tyr Glu Glu Lys Ser Tyr Thr Asp Gly Arg Arg Glu Asn Pro Cys
                1125                1130            1135

Glu Ser Asn Arg Gly Tyr Gly Asp Tyr Thr Pro Leu Pro Ala Gly Tyr
            1140            1145            1150

Val Thr Lys Asp Leu Glu Tyr Phe Pro Glu Thr Asp Lys Val Trp Ile
        1155            1160            1165

Glu Ile Gly Glu Thr Glu Gly Thr Phe Ile Val Asp Ser Val Glu Leu
    1170            1175            1180

Leu Leu Met Glu Glu
1185
```

BACILLUS THURINGIENSIS ISOLATES ACTIVE AGAINST PHTHIRAPTERA PESTS

DESCRIPTION

BACKGROUND OF THE INVENTION

Regular use of chemicals to control unwanted organisms can select for drug resistant strains. This has occurred in many species of economically important pests. The development of drug resistance necessitates a continuing search for new control agents having different modes of action.

Many hundreds of strains of *Bacillus thuringiensis* (B.t.) produce insecticidal toxins designated as delta endotoxins. They are synthesized by sporulating B.t. cells. When toxin is ingested by a susceptible insect, the cells of the gut epithelium are destroyed.

The reported activity spectrum of B.t. covers insect species within the orders Lepidoptera and Coleoptera, many of which are major pests in agriculture and forestry. The activity spectrum also includes the insect order Diptera, which includes mosquitoes and black flies. See Couch, T. L. (1980) "Mosquito Pathogenicity of *Bacillus thuringiensis* var. *israelensis,*" Developments in Industrial Microbiology 22:61-76; Beegle, C. C. (1978) "Use of Entomogenous Bacteria in Agroecosystems," Developments in Industrial Microbiology 20:97-104. Two varieties of B.t. known to kill mosquitos and blackflies are B.t. israelensis (B.t.i.) (Goldberg, L. J., J. Margalit [1977] Mosquito News 37:355-358) and B.t. morrisoni (B.t.m.) (Padua, L. E., M. Ohba, K. Aizawa [1984] J. Invertebrate Pathology 44:12-17). These are not harmful to non-target organisms (Mulla, M. S., B. A. Federici, H. A. Darwazeh [1982] Environmental Entomology 11:788-795), and play an important role in the integrated management of dipteran pests. They are safe to use in urban areas, and can be used in aquatic environments without harm to other species. Dipteran insects are serious nuisances as well as being vectors of many serious human and animal diseases such as malaria, onchocerciasis, equine encephalitis, and dog heartworm.

A small number of research articles have been published about the effects of δ-endotoxins from *B. thuringiensis* species on the viability of nematode eggs. Bottjer, Bone, and Gill (Experimental Parasitology 60:239-244, 1985) have reported that B.t. kurstaki and B.t. israelensis were toxic in vitro to eggs of the nematode *Trichostrongylus colubriformis*. In addition, 28 other B.t. strains were tested with widely variable toxicities. Ignoffo and Dropkin (Ignoffo, C. M. and Dropkin, V. H. [1977] J. Kans. Entomol. Soc. 50:394-398) have reported that the thermostable toxin from *Bacillus thuringiensis* (beta exotoxin) was active against certain nematodes. Beta exotoxin is a generalized cytotoxic agent with little or no specificity. Also, H. Ciordia and W. E. Bizzell (Jour. of Parasitology 47:41 [abstract] 1961) gave a preliminary report on the effects of *B. thuringiensis* on some cattle nematodes.

Sheep lice belong to the order of insects known as biting lice [Phthiraptera, suborder Mallophaga]. Some of the most common and economically important species of lice on mammals belong to the genus Damilinia which have sheep, cattle, goats and equines as their hosts. The general life span of these insects is about a month during which time the female lays 200-300 operculate eggs ("nits"). These are usually whitish in color and glued to the hair. There is no true metamorphosis but after about three moults a fully grown adult is present. The Mallophagans are equipped for biting and chewing. They ingest the outer layers of the hair shafts dermal scales, and blood scabs on mammals.

The genus Damilinia contains species which are capable of rapid population expansion by changing to asexual reproduction by parthenogenesis. Other important genera in Mallophaga include Felicola which are parasites on cats, and Trichodectes and Heterodoxus both of which utilize dogs as their hosts.

A closely related suborder is Anoplura which are sucking lice occuring solely on mammalian hosts. They have very similar life cycles but have piercing mouthparts allowing them to feed on the blood of cattle, pigs, equines, goats, and dogs. Economic genera within this suborder include Haematopinus, Linognathus, and Solenopotes.

*Damilinia ovis*, the biting louse of sheep, is more active than Linognathus and roams throughout the wool over the sheep's body. Damilinia can produce great irritation causing the sheep to become restless and have their grazing interrupted. Their condition deteriorates and in response to the irritation, the sheep rub against posts and wires which damage the fleece and also causes wool loss. When these lice bite there is an exudate of serum from the damaged skin on which the lice also feed. Heavy feeding increases the amount of exudate which causes two problems: the wool matts, reducing the value of the wool clipped and sheep blowflies, attracted by the damaged fleece and skin and louse feces, can cause strikes placing the animal at even higher risk.

Lice are normally treated by dipping, spraying, or drenching with insecticides containing synthetic chemical pesticides such as pyrethroids or avermectins.

At the present time there is a need to have more effective means to control lice that cause considerable damage to susceptible hosts. Advantageously, such effective means would employ biological agents.

BRIEF SUMMARY OF THE INVENTION

The subject invention concerns isolates and toxins of *Bacillus thuringiensis* which have activity against Phthiraptera pests. Specifically, *Bacillus thuringiensis* isolates have been found to be toxic to *Damilinia ovis*, the biting louse of sheep.

The B.t. isolates used according to the subject invention can be grown and the δ-endotoxin that is produced recovered by standard procedures as further described herein. The recovered toxin, the B.t. isolates themselves, or transformed microbes which produce the B.t. toxin can be formulated using standard procedures associated with the use of lice-killing products.

Among the B.t. isolates which can be used according to the subject invention are B.t. PS192N1, B.t. PS36A, B.t. PS71M3, B.t. PS81F, B.t. PS92J, B.t. PS40D1, B.t. PS204G6, B.t. PS81I, B.t. PS81GG, B.t. PS201T6, B.t. PS84C3, B.t. PS211B3, B.t. PS91C2, B.t. PS86A1 and B.t. PS192M4. The Bacillus thuringiensis isolate or toxins therefrom can preferably be utilized as drench.

The subject invention further concerns the use of genes cloned from *Bacillus thuringiensis* isolates. Specifically exemplified herein are genes cloned from B.t. isolates PS86A1, PS40D1, PS81F, PS81GG, and PS81I. The genes encode *Bacillus thuringiensis* δ-endotoxins which are active against lice. The genes can be transferred to suitable hosts via a recombinant DNA vector.

The transformed hosts which express the toxins can be used in methods to control lice. Also, the toxins expressed by these microbes can be recovered and used in lice control procedures.

BRIEF DESCRIPTION OF THE DRAWINGS

FIG. 1 is a photograph of a 10% SDS polyacrylamide gel showing alkalisoluble proteins from several B.t. isolates.

FIG. 2 is a photograph of a 10% SDS polyacrylamide gel showing alkalisoluble proteins from several B.t. isolates.

BRIEF DESCRIPTION OF THE SEQUENCES

SEQ ID NO. 1 is the nucleotide sequence for B.t. PS86A1.

SEQ ID NO. 2 is the amino acid sequence for B.t. PS86A1.

SEQ ID NO. 3 is the nucleotide sequence for B.t. PS40D1.

SEQ ID NO. 4 is the amino acid sequence for B.t. PS40D1.

SEQ ID NO. 5 is the nucleotide sequence for B.t. PS81F.

SEQ ID NO. 6 is the amino acid sequence for B.t. PS81F.

SEQ ID NO. 7 is the nucleotide sequence for B.t. PS81GG.

SEQ ID NO. 8 is the amino acid sequence for B.t. PS81GG.

SEQ ID NO. 9 is the nucleotide sequence for the toxin gene 81IA from B.t. PS81I.

SEQ ID NO. 10 is the amino acid sequence for the toxin gene 81IA from B.t. PS81I.

SEQ ID NO. 11 is the nucleotide sequence for the toxin gene 81IA2 from B.t. PS81I.

SEQ ID NO. 12 is the amino acid sequence for the toxin gene 81IA2 from B.t. PS81I.

SEQ ID NO. 13 is the nucleotide sequence for the toxin gene 81IB from B.t. PS81I.

SEQ ID NO. 14 is the amino acid sequence for the toxin gene 81IB from B.t. PS81I.

SEQ ID NO. 15 is the nucleotide sequence for the toxin gene 81IB2 from B.t. PS81I.

SEQ ID NO. 16 is the amino acid sequence for the toxin gene 81IB2 from B.t. PS81I.

DETAILED DISCLOSURE OF THE INVENTION

The B.t. isolates of the subject invention, and mutants thereof, can be cultured using standard known media and fermentation techniques. Upon completion of the fermentation cycle, the bacteria can be harvested by first separating the B.t. spores and crystals from the fermentation broth by means well known in the art. The recovered B.t. spores and crystals can be formulated into a drench, an aqueous spray, a bait, a cream, a wettable powder, a liquid concentrate, granules or other formulations by the addition of surfactants, dispersants, inert carriers and other components to facilitate handling and application for particular target pests. The formulation and application procedures are all well known in the art and are used with commercial strains. The B.t. isolates, and mutants thereof, can be used to control Phthiraptera pests.

As described herein, B.t. isolates of the invention have activity against sheep lice. It is expected that these isolates would be active against other lice as disclosed herein. Advantageously, the compositions and methods of the subject invention can be used to control biting lice from the suborders Mallophaga and Anoplura with particularly preferred targets being members of the Damilinia, Felicola, Trichodectes, Heterodoxus, Haematopinus, Linognathus and Solenopotes genera.

In a preferred embodiment, the compositions and methods of the subject invention are used to control *Damilinia ovis*.

B.t. Isolates. Isolates which can be used according to the subject invention have been deposited in the Agricultural Research Service Patent Culture Collection (NRRL), Northern Regional Research Center, 1815 North University Street, Peoria, Ill. 61604 USA.

| Culture | Accession No. | Deposit date |
| --- | --- | --- |
| Bacillus thuringiensis PS36A | NRRL B-18929 | December 27, 1991 |
| Bacillus thuringiensis PS40D1 | NRRL B-18300 | February 3, 1988 |
| Bacillus thuringiensis PS71M3 | NRRL B-18930 | December 27, 1991 |
| Bacillus thuringiensis PS81F | NRRL B-18424 | October 7, 1988 |
| Bacillus thuringiensis PS81GG | NRRL B-18425 | October 11, 1988 |
| Bacillus thuringiensis PS81I | NRRL B-18484 | April 19, 1989 |
| Bacillus thuringiensis PS84C3 | NRRL B-18399 | August 16, 1988 |
| Bacillus thuringiensis PS86A1 | NRRL B-18400 | August 16, 1988 |
| Bacillus thuringiensis PS91C2 | NRRL B-18931 | December 27, 1991 |
| Bacillus thuringiensis PS92J | NRRL B-18747 | January 9, 1991 |
| Bacillus thuringiensis PS192M4 | NRRL B-18932 | December 27, 1991 |
| Bacillus thuringiensis PS192N1 | NRRL B-18721 | October 5, 1990 |
| Bacillus thuringiensis PS201T6 | NRRL B-18750 | January 9, 1991 |
| Bacillus thuringiensis PS204G6 | NRRL B-18686 | July 17, 1990 |
| Bacillus thuringiensis PS211B2 | NRRL B-18921 | November 15, 1991 |
| E. coli (DH5α(pMYC386)) | NRRL B-18423 | October 7, 1988 |
| E. coli (pMYC388) | NRRL B-18428 | October 19, 1988 |
| P. fluorescens (pM3, 130-7) | NRRL B-18332 | February 22, 1988 |

The toxin genes used according to the subject invention can be obtained, for example, from the *B. thuringiensis* isolate designated PS81I. As shown above, a subculture of PS81I harboring the toxin genes of the invention has been deposited.

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. These deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a a period of at least thirty (30) years after the date of deposit or for the enforceable life of any patent which may issue disclosing a culture. The depositor acknowledges the duty to replace a deposit should the depository be unable to furnish a sample when requested, due to the condition of a deposit. All restrictions on the availability to the public of the subject culture deposits will be irrevocably removed upon the granting of a patent disclosing them.

Each of the deposited strains which can be used according to the subject invention share certain morphological characteristics which may be of interest to the skilled artisan practicing the invention. For example, for each of the isolates described herein the colony morphology is a large colony with a dull surface, typical of B.t.. Culture methods as well as vegetative cell morphology are also typical of B.t..

Of course, the various isolates of the subject invention can be ordered individually from NRRL. Also, these isolates are distinguishable using standard procedures. The specific characteristics of these isolates are presented in Table 1. Table 1. Characteristics of the B.t. strains of the subject invention.

| B.t. strain | Inclusion type | Approx. M.W. of Proteins (kDa) | Serotype |
|---|---|---|---|
| PS40D1 | flat square | 72, 64 | |
| PS84C3 | amorphic | 105, 70, 41, 37, 36, 35 | |
| PS86A1 | multiple amorphic | 58, 45 | |
| PS92J | amorphic | 102, 81, 67 | |
| PS192N1 | amorphic | 140, 122, 76, 72, 38 | |
| PS201T6 | elliptical & bipyramid | 133, 31 | |
| PS204G6 | long amorphic | 23, 21 | |
| PS211B2 | multiple amorphic | 105, 70, 41, 37, 36, 35 | |
| PS71M3 | amorphic | 142, 133, 67, 27 | 8a8b |
| PS36A | bipyramid | 130, 60 | 3a3b* |
| PS81GG | bipyramid | 130, 60 | 3a3b* |
| PS192M4 | bipyramid | 130, 60 | 4a4b |
| PS81F | bipyramid | 130, 60 | 4a4c |
| PS81I | bipyramid | 130 | 7 |
| PS91C2 | bipyramid | 130 | 8 |

*These three strains can be distinguished by RFLP (see Example 9).

Mutants of the isolates of the invention can be made by procedures well known in the art. For example, an asporogenous mutant can be obtained through ethylmethane sulfonate (EMS) mutagenesis of an isolate. Alternatively, the mutants can be made using ultraviolet light and nitrosoguanidine by procedures well known in the art.

A small percentage of the asporogenous mutants will remain intact and not lyse for extended fermentation periods; these strains are designated lysis minus (—). Lysis minus strains can be identified by screening asporogenous mutants in shake flask media and selecting those mutants that are still intact and contain toxin crystals at the end of the fermentation. Lysis minus strains are suitable for a cell fixation process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

Transformation of Microbial Hosts. The toxin genes harbored by the novel isolates of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of the target pests where they will proliferate and be ingested by the pests. The result is a control of the target lice. Alternatively, the microbe hosting the toxin gene can be treated under conditions that prolong the activity of the toxin produced in the cell. The treated cell then can be applied to the environment of target pest(s). The resulting product retains the toxicity of the B.t. toxin.

When the B.t. toxin gene is introduced via a suitable vector into a microbial host, and said host is applied to the environment in a living state, it is advantageous to use microorganism hosts which are known to occupy the environment of the pest. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

A wide variety of ways are available for introducing a B.t. gene expressing a toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site appropriate for the host and an initiation codon will be present.

Various manipulations may be employed for enhancing the expression of the messenger RNA, particularly by using an active promoter, as well as by employing sequences, which enhance the stability of the messenger RNA. The transcriptional and translational termination region will involve stop codon(s), a terminator region, and optionally, a polyadenylation signal. A hydrophobic "leader" sequence may be employed at the amino terminus of the translated polypeptide sequence in order to promote secretion of the protein across the inner membrane.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 5000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competetive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The B.t. gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers is may be present, which have been described previously. Where integration is desired, the plasmid will desirably include a sequence homologous with the host genome.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| Phenylalanine (Phe) | TTK | Histidine (His) | CAK |
|---|---|---|---|
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.

A=adenine
G=guanine
C=cytosine
T=thymine
X=T or C if Y is A or G
X=C if Y is C or T
Y=A, G, C or T if X is C
Y=A or G if X is T
W=C or A if Z is A or G
W−C if Z is C or T
Z=A, G, C or T if W is C
Z=A or G if W is A
QR=TC if S is A, G, C or T; alternatively QR=AG if S is T or C
J=A or G
K=T or C
L=A, T, C or G
M=A, C or T The above shows that the novel amino acid sequence of the B.t. toxins can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249–255). Thus, the subject invention includes mutants of the amino acid sequence depicted herein which do not alter the protein secondary structure, or if the structure is altered, the biological activity is substantially retained. Further, the invention also includes mutants of organisms hosting all or part of a toxin encoding a gene of the invention. Such microbial mutants can be made by techniques well known to persons skilled in the art. For example, UV irradiation can be used to prepare mutants of host organisms. Likewise, such mutants may include asporogenous host cells which also can be prepared by procedures well known in the art.

Transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae, Actinomycetales, and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Additional host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., Streptomyces sp., Streptococcus, Staphylococcus, Proteus and the like. Specific organisms include *Pseudomonas aeruginosa, Pseudomonas fluorescens, Saccharomyces cerevisiae, Bacillus thuringiensis, Escherichia coli, Bacillus subtilis, Streptomyces lividans* and the like.

The cell will usually be intact and be substantially in the proliferative form when treated, rather than in a spore form, although in some instances spores may be employed.

Treatment of Cells. Microbes containing a B.t. toxin gene can be treated to enhance stability, longevity, duration, etc. Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Lugol iodine, Bouin's fixative, and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

Formulations. The B.t. cells may be formulated in a variety of ways. In a preferred embodiment the B.t. cells or the toxin is applied as a drench. Alternative formulations include wettable powders, granules or dusts, and mixtures with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The B.t. toxins of the invention can be administered as a liquid drench when used against lice on sheep and other Phthiraptera pests. The drench is normally a solution, suspension or dispersion of the active ingredient, usually in water, together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight.

Where it is desired to administer the toxin compounds in a dry form, these forms are prepared by intimately and uniformly mixing the active ingredient with suitable finely divided diluents, fillers, disintegrating agents and/or binders such as starch, lactose, talc, magnesium stearate, vegetable gums and the like. Such formulations may be varied widely with respect to their total weight and content of the antiparasitic agent, depending upon the factors such as the type of host animal to be treated, the severity and type of infection and the weight of the host.

The pesticidal concentration will vary depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg.

The formulations can be applied to the environment of the lice by applying directly to the coat of the animal.

The methods and compositions of the subject invention can be used to control lice, which can parasitize vertebrates. Specifically, the invention can be used to control lice in humans, livestock, domestic pets, and other animals. As used herein, the term "livestock" can include, for example, sheep, cattle, pigs, and goats. The methods and compositions of the subject invention may be used to control immature and adult lice. The methods of control include, but are not limited to, direct application to the animal coat. The B.t. toxins described herein may be used alone, or in rotation or combination with other anti-lice chemicals.

Following are examples which illustrate procedures, including the best mode, for practicing the invention. These examples should not be construed as limiting. All percentages are by weight and all solvent mixture proportions are by volume unless otherwise noted.

Example 1-Culturing of the Novel B.t. Isolates

A subculture of the novel B.t. isolates, or mutants thereof, can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and/or crystals, obtained in the above fermentation, can be isolated by procedures well known in the art. A frequently-used procedure is to subject the harvested fermentation broth to separation techniques, e.g., centrifugation.

Example 2-Isolation of Genes and Determination of N-Terminus Sequences

The *B. thuringiensis* isolate can be cultured as described in Example 1. The parasporal inclusion bodies (toxin crystals) partially purified by sodium bromide (26-40%) isopycnic gradient centrifugation (Pfannestiel, M. A., E. J. Ross, V. C. Krammer, and K. W. Nickerson [1984] FMES Microbiol. Lett. 31:39).

Toxic proteins can be bound to PVDF membranes (Millipore, Bedford, Mass.) by western blotting techniques (Towbin, H., T. Staehlelin, and K. Gordan [179] Proc. Natl. Acad. Sci. USA 76:4350) and the N-terminal amino acid sequences determined by the standard Edman reaction with an automated gas-phase sequenator (Hunkapiller, M. W., R. M. Hewick, W. L. Dreyer, and L. E. Hood [1983] Meth. Enzymol. 91:399).

From this sequence data oligonucleotide probes can be designed by utilizing a codon frequency table assembled from available sequence data of other B.t. toxin genes. The probes can be synthesized on an Applied Biosystems, Inc. DNA synthesis machine.

Protein purification and subsequent amino acid analysis of the N-terminal peptide can be used to identify oligonucleotide probes for the isolation of toxin genes from B.t. isolates. RFLP analysis of restricted total cellular DNA using radiolabeled oligonucleotide probes facilitates the identification of different genes or gene fragments. For example, the following N-terminus sequences have been identified:

| Strain | Approx. M.W. of Protein | Sequence |
| --- | --- | --- |
| PS192N1 | 38 kDa | AIIDIEQSIYKYMDW |
| PS201T6 | 31 kDa | MKESIYYNEE |
| PS204G6 | 23 kDa | GNFNXEKDYD |

Example 3-Growth of B.t. PS81F (NRRL B-18424)

PS81F was grown at 30° C. on a rotary shaker at 200 rpm in 21 baffled flasks containing 400 ml of broth for 64 hours. The broth medium contained Bacto peptone, 7.5 g/l; glucose, 1.0 g/l; $KH_2PO_4$, 3.4 g/l; $K_2HPO_4$, 4.35 g/l; "salt solution," 5.0 ml; and "$CaCl_2$ solution," 5.0 ml. The salt and $CaCl_2$ solutions were filter sterilized and added to the autoclaved broth at the time of inoculation. The "salt solution" contained in 100 ml: $MgSO_4$-$7H_2O$, 2.46 g; $MnSO_4$-$H_2O$, 0.04 g; $ZnSO_4$-$7H_2O$, 0.28 g; and $FeSO_4$-$7H_2O$, 0.40 g. The "calcium solution" contained in 100 ml at pH 7.2: $CaCl_2$-$H_2O$, 3.66 g. B.t. spores and crystals obtained by the above fermentation were isolated by centrifugation at 7000 g for 20 minutes. Purification of the δ-endotoxin inclusions of various B.t. isolates was accomplished by banding the inclusions in NaBr density gradients according to the method of Pfannensteil, Ross, Kramer, and Nickerson ([1984] FEMS Microbiol. Lett. 21:39).

Example 4-Cloning of PS81F Toxin Gene and Transformation into *Escherichia coli*

Total cellular DNA was prepared by growing the cells of B.t. PS81F to a low optical density ($OD_{600}$=1.0) and recovering the cells by centrifugation. The cells were protoplasted in TES buffer (30 mM Tris-Cl, 10 mM EDTA, 50 mM NaCl, pH=8.0) containing 20% sucrose and 50 mg/ml lysozyme. The protoplasts were lysed by addition of SDS to a final concentration of 4%. The cellular material was precipitated overnight at 4° C. in 100 mM final concentration neutral potassium chloride. The supernate was extracted twice with phenol/chloroform (1:1). The DNA was precipitated in ethanol and purified by isopycnic banding on a cesium chloride gradient.

Total cellular DNA from PS81F was digested with EcoRI and separated by electrophoresis on a 0.8% Agarose-TAE-buffered gel. A Southern blot of the gel was probed with the NsiI to NsiI fragment of the toxin gene contained in plasmid pM3,130-7 of NRRL B-18332 and the NsiI to KpnI fragment of the "4.5 Kb class" toxin gene (Kronstad and Whitely [1986] Gene USA 43:29-40). A 3.5 Kb hybridizing band in PS81F was detected.

Two hundred micrograms of PS81F total cellular DNA was digested with EcoRI and separated by electrophoresis on a preparative 0.8% Agarose-TAE gel. The 3.0 Kb to 4.0 Kb region of the gel was cut out and the DNA from it was electroeluted and concentrated using an ELUTIP™-d (Schleicher and Schuell, Keene, N.H.) ion exchange column. The isolated EcoRI fragments were ligated to LAMBDA ZAP™ EcoRI arms (Stratagene Cloning Systems, La Jolla, Calif.) and packaged using GIGAPACK GOLD™ extracts. The packaged recombinant phage were plated with *E. coli* strain BB4 (Stratagene) to give high plaque density. The plaques were screened by standard nucleic acid hybridization procedure with radiolabeled probe. The plaques that hybridized were purified and re-screened at a lower plaque density. The resulting purified phage were grown with R408 M13 helper phage (Stratagene) and the recombinant BLUESCRIPT™ (Stratagene) plasmid was automatically excised and packaged. The "phagemid" was re-infected in XL1-Blue *E. coli* cells (Stratagene) as part of the automatic excision process. The infected XL1-Blue cells were screened for ampicillin resistance and the resulting colonies were analyzed by standard miniprep procedure to find the desired plasmid. The plasmid, designated pM5,31-1, contained an approximate 3.5 Kb EcoRI insert and was sequenced using Stratagene's T7 and T3 primers plus a set of existing B.t. endotoxin oligonucleotide primers. About 1.7 Kb of the toxin gene was sequenced and data analysis comparing PS81F to other cloned B.t. endotoxin genes showed that the PS81F (SEQ ID NOS. 5 and 6) sequence was unique. A synthetic oligonucleotide (GCTGAAGAACTTCCTATTCGTGGTGGTGAGC) was constructed to one of the regions in the PS81F sequence (SEQ ID NO. 5) that was least homologous relative to other existing B.t. endotoxin genes.

Total cellular DNA partially digested with Sau3A and fractionated by electrophoresis into a mixture of 9-23 Kb fragments on a 0.6% agarose TAE gel was ligated into LAMBDA DASH™ (Stratagene). The packaged phage were plated out with P2392 *E. coli* cells (Stratagene) at a high titer and screened using the radiolabeled synthetic oligonucleotide supra as a nucleic acid hybridization probe. Hybridizing plaques were rescreened at a lower plaque density. A purified hybridizing plaque was used to infect P2392 *E. coli* cells in liquid culture for preparation of phage for DNA isolation. DNA was isolated by standard procedures. Preparative amounts of recombinant phage DNA were digested with SalI (to release the inserted DNA from lambda arms) and separated by electrophoresis on a 0.6% Agarose-TAE gel. The large fragments (electroeluted and concentrated as described above) were ligated to an XhoI digested and phosphatased BLUESCRIPT™ plasmid. The ligation was transformed into *E. coli* DH5(α) competent cells (BRL) and plated on LB agar containing ampicillin, isopropyl-(β)-D-thiogalactoside (IPTG) and 5-bromo-4-chloro-3-indolyl-(β)-D-galactoside (XGAL). White colonies (with insertions in the (β)-galactosidase gene of pBluescript) were subjected to standard miniprep procedures to isolate the plasmid, designated pMI,43-24. The full length toxin gene was sequenced by using oligonucleotide primers made to the "4.3 Kb class" toxin gene and by "walking" with primers made to the sequence of PS81F (SEQ ID NOS. 5 and 6).

The plasmid pM1,43-24 contains about 18 Kb of PS81F DNA including the 3.518 Kb which codes for the 133,266 dalton endotoxin. The plasmid was reduced in size by cutting out approximately 13 Kb of non-coding DNA, ligating the ends transforming DH5(α) and plating on LB agar containing ampicillin. The resulting colonies were analyzed by standard miniprep procedures to isolate plasmids that were reduced in size. The desired plasmid, pMYC386, contains the coding sequence of the PS81F toxin gene, which could be excised as an SaeI to ApaI 4.5 Kb fragment.

The above cloning procedures were conducted using standard procedures unless otherwise noted.

The various methods employed in the preparation of the plasmids and transformation of host organisms are well known in the art. Also, methods for the use of lambda bacteriophage as a cloning vehicle, i.e., the preparation of lambda DNA, in vitro packaging, and transfection of recombinant DNA, are well known in the art. These procedures are all described in Maniatis, T., Fritsch, E. F., and Sambrook, J. (1982) Molecular Cloning: A Laboratory Manual, Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased form Bethesda Research Laboratories, Gaithersburg, Md., or New England Biolabs, Beverly, Mass. The enzymes are used according to the instructions provided by the supplier.

Plasmid pMYC386 containing the B.t. toxin gene, can be removed from the transformed host microbe by use of standard well-known procedures. For example, *E. coli* NRRL B-18423 can be subjected to cleared lysate isopycnic density gradient procedures, and the like, to recover pMYC386. The nucleotide sequence encoding the B.t. toxin PS81F is shown in SEQ ID NO. 1. The deduced amino acid sequence is shown in SEQ ID NO. 2.

Example 5-Molecular Cloning of Gene Encoding a Novel Toxin from *Bacillus thuringiensis* Strain PS86A1

Total cellular DNA was prepared from PS86A1 cells grown to an optical density, at 600 nm, of 1.0. Cells were pelleted by centrifugation and resuspended in protoplast buffer (20 mg/ml lysozyme in 0.3M sucrose, 25 mM Tris-Cl, pH 8.0, 25 mM EDTA). After incubation at 37° C. for 1 hour, protoplasts were lysed by two cycles of freezing and thawing. Nine volumes of a solution of 0.1M NaCl, 0.1% SDS, 0.1M Tris-Cl were added to complete lysis. The cleared lysate was extracted twice with phenol:chloroform (1:1). Nucleic acids were precipitated with two volumes of ethanol and pelleted by centrifugation. The pellet was resuspended in 10 mM Tris-Cl, 1 mM EDTA (TE), pH 8.0, and RNAse was added to a final concentration of 50 µg/ml. After incubation at 37° C. for 1 hour, the solution was extracted once each with phenol:chloroform (1:1) and TE-saturated chloroform. DNA was precipitated from the aqueous phase by the addition of one-tenth volume of 3M NaOAc and two volumes of ethanol. DNA was pelleted by centrifugation, washed with 70% ethanol, dried, and resuspended in TE.

Restriction fragment length polymorphism (RFLP) analyses were performed by standard hybridization of southern blots of PS86A1 DNA with a $^{32}$P-labeled oligonucleotide probe designated as 86A1-A. The sequence of the 86A1-A probe was:

```
5' ATG ATT GAT TCT AAA ACA ACA TTA
CCA AGA CAT TCT/A TTA ATT/A CAT
ACT/A ATT/A AA 3'
```

The probe was mixed at four positions, as shown. Hybridizing bands included an approximately 3.6 kbp HindIII fragment and an approximately 9.3 kbp EcoRV fragment.

A gene library was constructed from PS86A1 DNA partially digested with Sau3A. Partial restriction digests were fractionated by agarose gel electrophoresis. DNA fragments 6.6 to 23 kbp in size were excised from the gel, electroeluted from the gel slice, and recovered by ethanol precipitation after purification on an Elutip-D ion exchange column. The Sau3A inserts were ligated into BamHI-digested LambdaGem-11 (Promega, Madison, Wis.). Recombinant phage were packaged and plated on *E. coli* KW251 cells (Promega). Plaques were screened by hybridization with the radiolabeled 86A1-A oligonucleotide probe. Hybridizing phage were plaque-purified and used to infect liquid cultures of *E. coli* KW251 cells for isolation of phage DNA by standard procedures (Maniatis et al. [1982] Molecular Cloning: A Laboratory Manual, Cold Spring Harbor Laboratory, Cold Spring Harbor, N.Y.). For subcloning, preparative amounts of DNA were digested with EcoRI and SalI, and electrophoresed on an agarose gel. The approximately 2.9 kbp band containing the toxin gene was excised from the gel, electroeluted from the gel slice, and purified by ion exchange chromatography as above. The purified DNA insert was ligated into EcoRI+SalI-digested pHTBlueII (an *E. coli*/B.t. shuttle vector comprised of pBlueScript S/K (Stratagene, San Diego, Calif.) and the replication origin from a resident B.t. plasmid (D. Lereclus et al. [1989] FEMS Microbiol. Lett. 60:211–218). The ligation mix was used to transform frozen, competent *E. coli* NM522 cells (ATCC 47000). Transformants were plated on LB agar (Maniatis et al., supra) containing ampicillin, isopropyl-(β)-D-thiogalactoside (IPTG), and 5-bromo-4-chloro-3-indolyl-(β)-D-galactoside (XGAL). Plasmids were purified from putative recombinants by alkaline lysis (Maniatis et al., supra) and analyzed by electrophoresis of EcoRI and SalI digests on agarose gels. The desired plasmid construct, pMYC2320, contains the novel toxin gene of the invention. The DNA sequence of this gene is shown in SEQ ID NO. 1. The novel toxin expressed by this gene is shown in SEQ ID NO. 2.

Plasmid pMYC2320 was introduced into an acrystalliferous (Cry−) B.t. host (B.t. HD-1 Cry B, A. I. Aronson, Purdue University, West Lafayatte, Ind.) by electroporation. Expression of an approximately 58 kDa protein is verified by SDS-PAGE analysis and activity against the alfalfa weevil.

The restriction enzymes disclosed herein can be purchased from Bethesda Research Laboratories, Gaithersburg, Md. or New England Biolabs, Beverly, Mass. The enzymes are used according to the instructions provided by the supplier.

Plasmid pMYC2320 containing the B.t. toxin gene, can be removed from the transformed host microbe by use of standard well-known procedures. For example, *E. coli* NM522 (pMYC2320) can be subjected to cleared lysate isopycnic density gradient procedures, and the like, to recover pMYC2320.

Example 6-Cloning of PS81GG Toxin Gene and Transformation into *Escherichia coli*

Total cellular DNA was prepared by growing the cells of B.t. PS81GG to a low optical density (OD$_{600}$=1.0) and recovering the cells by centrifugation. The cells were protoplasted in TES buffer (30 mM Tris-Cl, 10 mM EDTA, 50 mM NaCl, pH=8.0) containing 20% sucrose and 50 mg/ml lysozyme. The protoplasts were lysed by addition of SDS to a final concentration of 4%. The cellular material was precipitated overnight at 4° C. in 100 mM final concentration neutral potassium chloride. The supernate was phenol/chloroform (1:1) extracted twice and the DNA precipitated in ethanol. The DNA was purified by isopycnic banding on a cesium chloride gradient.

Total cellular DNA from PS81GG was digested with EcoRI and separated by electrophoresis on a 0.8% Agarose-TAE-buffered gel. A Southern blot of the gel was probed with the NsiI to NsiI fragment of toxin gene contained in the plasmid pM1,130-7 of NRRL B-18332 and the NsiI to KpnI fragment of the "4.5 Kb class" toxin gene (Kronstad and Whitely, [1986] Gene U.S.A. 43:29-40). These two fragments were combined and used as the probe. A 3.0 Kb hybridizing band in PS81GG was detected.

Two hundred micrograms of PS81GG total cellular DNA was digested with EcoRI and separated by electrophoresis on a preparative 0.8% Agarose-TAE gel. The 2.5 to 3.5 Kb region of the gel was cut out and the DNA from it was electroeluted and concentrated using an ELUTIP TM -d (Schleicher and Schuell, Keene, NH) ion exchange column. The isolated EcoRI fragments were ligated to LAMBDA ZAP TM EcoRI arms (Stratagene Cloning Systems, La Jolla, Calif.) and packaged using GIGAPACK GOLD TM extracts. The packaged recombinant phage were plated out with *E. coli* strain BB4 (Stratagene) to give high plaque density. The plaques were screened by standard nucleic acid hybridization procedure with radiolabeled probe. The plaques that hybridized were purified and re-screened at a lower plaque density. The resulting purified phage were grown with R408 M13 helper phage (Stratagene) and the recombinant BLUESCRIPT TM (Stratagene) plasmid was automatically excised and packaged. The "phagemid" was re-infected in XL1-Blue *E. coli* cells (Stratagene) as part of the automatic excision process. The infected XL1-Blue cells were screened for ampicillin resistance and the resulting colonies were analyzed by standard miniprep procedure to find the desired plasmid. The plasmid, pM4,31-1, contained an approximate 3.0 Kb EcoRI insert which contained an internal EcoRI site. The cloned fragment was sequenced using Stratagene's T7 and T3 primers plus a set of existing B.t. endotoxin oligonucleotide primers.

Total cellular PS81GG DNA (SEQ ID NO. 7) was partially digested with AluI or RsaI and digests were mixed. DNA was modified with EcoRI methylase, EcoRI linkers were ligated onto ends, and excess linkers were removed by EcoRI digestion. DNA was size-fractionated on 0.8% Agarose-TAE gels and the approximately 4 to 8 Kb fragments were recovered by electroelution and NACS 52 column chromatography (BRL). Following insert ligation into LAMBDA ZAP™ (Stratagene) which was cut with EcoRI, DNA was packaged into phage heads. Libraries were screened by nucleic acid filter hybridization using a radiolabeled synthetic oligonucleotide probe (CCTGTCGGTTTTTCGGGGCC).

Hybridizing positives were plaque-purified and insert DNA was excised from phage DNA onto pBLUESCRIPT™ plasmid (Stratagene) with helper phage, according to manufacturers directions (Stratagene). The desired plasmid, pMYC388, was restriction mapped and the B.t. toxin coding sequence fully characterized by DNA sequencing.

The above cloning procedures were conducted using standard procedures unless otherwise noted.

The various methods employed in the preparation of the plasmids and transformation of host organisms are well known in the art. Also, methods for the use of lambda bacteriophage as a cloning vehicle, i.e., the preparation of lambda DNA, in vitro packaging, and transfection of recombinant DNA, are well known in the art. These procedures are all described in Maniatis, T., Fritsch, E. F., and Sambrook, J. (1982) Molecular Cloning: A Laboratory Manual, Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Bethesda Research Laboratories, Gaithersburg, Md., or New England Biolabs, Beverly, Mass. The enzymes are used according to the instructions provided by the supplier.

Plasmid pMYC388 containing the B.t. toxin gene, can be removed from the transformed host microbe by use of standard well-known procedures. For example, *E. coli* (pMYC388) NRRL B-18428 can be subjected to cleared lysate isopycnic density gradient procedures, and the like, to recover pMYC388. The nucleotide sequence encoding B.t. toxin PS81GG is shown in SEQ ID NO. 7. The deduced amino acid sequence is shown in SEQ ID NO. 8.

Example 7-Cloning of Toxin Genes From Isolate PS81I and Transformation into *Escherichia coil*

Total cellular DNA was prepared from B.t. PS81I cells grown to a low optical density ($OD_{600}$=1.0). The cells were recovered by centrifugation and protoplasted in TES buffer (30 mM Tris-Cl, 10 mM ethylenediaminetetraacetic acid [EDTA], 50 mM NaCl, pH=8.0) containing 20% sucrose and 50 mg/ml lysozyme. The protoplasts were lysed by addition of sodium dodecyl sulfate (SDS) to a final concentration of 4%. The cellular material was precipitated overnight at 4° C. in 100 mM (final concentration) neutral potassium chloride. The supernate was extracted twice with phenol/chloroform (1:1). The DNA was precipitated with ethanol and purified by isopycnic banding on a cesium gradient.

Total cellular DNA from PS81I was digested with EcoRI and separated by electrophoresis on a 0.8% (w/v) Agarose-TAE (50 mM Tris-Cl, 20 mM NaOAc, 2.5 mM EDTA, pH=8.0) buffered gel. A Southern blot of the gel was hybridized with a [$^{32}$P] radiolabeled probe against the 3.2 Kb NsiI to NsiI fragment of the toxin gene contained in plasmid pM3, 130-7 of NRRL B-18332 and the 2.4 Kb NsiI to KpnI fragment of the "4.5 Kb class" toxin gene (Kronstad and Whitely [1986] Gene USA 43:29-40). These two fragments were combined and used as the probe. In the 1.5 Kb to 2.5 Kb size range, 2.3 Kb, 1.95 Kb, and 1.6 Kb hybridizing bands were detected in PS81I.

The following description outlines the steps taken in cloning two of the three EcoRI fragments described above. Two hundred micrograms of PS81I total cellular DNA was digested with EcoRI and separated by electrophoresis on a preparative 0.8% (w/v) Agarose-TAE gel. The 1.5 Kb to 2.3 Kb region of the gel was cut out and the DNA from it was electroeluted and concentrated using an ELUTIP™-d (Schleicher and Schuell, Keene, N.H.) ion exchange column according to the manufacturer's specification. The isolated EcoRI fragments were ligated to LAMBDA ZAP ™ EcoRI arms (Stratagene Cloning Systems, La Jolla, Calif.) and packaged using Gigapak GOLD ™ (Stratagene) extracts. The packaged recombinant phage were plated with *E. coli* strain BB4 (Stratagene) to give high plaque density. The plaques were screened by standard nucleic acid hybridization procedures with radiolabeled probe. The plaques that hybridized were purified and re-screened at a lower plaque density. The resulting purified phage were grown with R408 M13 helper phage (Stratagene) and the recombinant BlueScript ™ (Stratagene) plasmid was automatically excised and packaged. The "phagemid" was re-infected in XL1-Blue *E. coli* cells (Stratagene) as part of the automatic excision process. The infected XL1-Blue cells were screened for ampicillin resistance and the resulting colonies were analyzed by a standard rapid plasmid purification procedure to identify the desired plasmids. The plasmids, designated pM2,31-4 and pM2,31-1, contain approximately 1.95 Kb and 1.6 Kb EcoRI inserts, respectively. The DNA sequence of both inserts was determined using Stratagene's T7 and T3 oligonucleotide primers plus a set of existing internal B.t. endotoxin gene oligonucleotide primers. About 500 bp of the insert in pM2,31-4 was sequenced. In the same manner, approximately 1.0 Kb of the insert in pM2,31-1 was sequenced. Data analysis comparing the two sequences to other cloned and sequenced B.t. endotoxin genes showed that two distinct, unique partial toxin gene sequences had been found. Synthetic oligonucleotides were constructed to regions in both sequences that had minimum homology to other characterized B.t. endotoxin genes. The 42-mer oligonucleotide constructed to the sequence of the insert in pM2,31-4 was GGATACCGGTGACCCATTAACATTCCAATCTT TTAGTTACGC; it was used to isolate a toxin gene sequence called 81IA (SEQ ID NOS. 9 and 10). The 40-mer oligonucleotide constructed to the sequence of the insert in pM2,31-1 was GAAGTTTATGGCCTCTTTCTGTAGAAAATCAAATTGGACC; it was used to isolate a toxin gene sequence called 81IB (SEQ ID NOS. 13 and 14).

In order to clone both complete toxin genes, a Sau3A partial library was constructed. PS81I total cellular DNA partially digested with Sau3A and size fractionated by electrophoresis into a mixture of 9–23 Kb fragments on a 0.6% agarose-TAE gel, and purified as described previously, was ligated into LambdaGEM11™ (PROMEGA). The package phage were plated on P2392 *E. coli* cells (Stratagene) at a high titer and screened using the radiolabeled synthetic oligonucleotides (aforementioned) as nucleic acid hybridization probes. Hybridizing plaques, using each probe, were rescreened at a lower plaque density. Purified plaques that hybridized with either probe were used to infect P2392 *E. coli* cells in liquid culture for preparation of phage for DNA isolation. DNA was isolated by standard procedures. Preparative amounts of DNA were digested with SalI (to release the inserted DNA from lambda arms) and separated by electrophoresis on a 0.6% agarose-TAE gel. The large fragments, electroeluted and concentrated as described above, were ligated to SalI-digested and dephosphorylated pUC19 (NEB). The ligation mix was introduced by transformation into DH5($\alpha$) competent *E. coli* cells (BRL) and plated on LB agar containing ampicillin, isopropyl-($\beta$)-D-thiogalactoside (IPTG), and 5-bromo-4-chloro-3-indolyl-($\beta$)-D-galactoside (XGAL). White colonies, with prospective insertions in the ($\beta$)-galactosidase gene of pUC19, were subjected to standard rapid plasmid purification procedures to isolate the desired plasmids. Plasmid pM3,122-1 contains a 15 Kb Sau3A fragment isolated using the 81IA oligonucleotide probe. Plasmid pM4,59-1 contains an 18 Kb Sau3A fragment isolated using the 81IB oligonucleotide probe.

Plasmid pM3,122-1 was digested with several restriction enzymes and Southern blotted. The blot was probed with the [$^{32}$P] radiolabeled 81IA (SEQ ID NO. 9) specific oligonucleotide probe, as well as the labeled oligonucleotide sequencing primers made to known B.t.k. toxin genes. The resulting autoradiogram showed that two toxin genes were present in tandem on this cloned Sau3A fragment. Plasmid pM3,122-1 had a 4.0 Kb NdeI fragment that hybridized with oligonucleotide probes made to known B.t.k. genes. This fragment, however, did not hybridize with the specific oligonucleotides to 81IA or 81IB; a new toxin gene had been discovered and subsequently was called 81IA2 (SEQ ID NOS. 11 and 12). The 4.0 Kb NdeI fragment was isolated and cloned in pUC19, yielding plasmid pMYC392. The 81IA toxin gene (SEQ ID NOS. 9 and 10) was isolated by digesting pM3,122-1 with HindIII, with resulting deletion of most of the 81IA2 (SEQ ID NOS. 11 and 12) toxin gene. The fragment was recircularized to form pMYC1603. The 81IA toxin gene is unique based on its restriction map and its DNA sequence (SEQ ID NO. 9).

Plasmid pM4,59-1 was digested with several restriction enzymes and Southern blotted. The blot was probed with the [$^{32}$P] radiolabeled 81IB specific oligonucleotide probe (SEQ ID NO. 13), as well as with labeled oligonucleotide sequencing primers made to known B.t.k. toxin genes. The plasmid pM4,59-1 was mapped and found to contain only a partial 81IB toxin gene. The full open reading frame (ORF) of a second toxin gene was discovered on the 18 Kb fragment and called 81IB2 (SEQ ID NOS. 15 and 16). The 81IB2 toxin gene was cloned separately from the 81IB toxin gene (SEQ ID NO. 13) by digestion of pM4,59-1 with NdeI and SmaI, filling in the NdeI overhang and ligating the linear fragment back together. The resulting plasmid was called pMYC394. The full ORF of the 81IB toxin gene was isolated from another Sau3A fragment, cloned from the lambda library, on a 7.3 Kb HindIII fragment in pBluescript (Stratagene). The resulting plasmid is pMYC393.

The toxin genes were sequenced by the standard Sanger dideoxy chain termination method using oligonucleotide primers made to the "4.5 Kb class" toxin gene and by "walking" with primers made to the sequences of the new toxin genes. Sequence analysis of the four toxin genes has elucidated unique open reading frames and has deduced unique endotoxin proteins. The following table summarizes the size of each ORF in base pairs and the deduced endotoxin molecular weight in daltons.

| TOXIN GENE | ORF (bp) | DEDUCED MW (daltons) | SEQUENCE ID |
|---|---|---|---|
| 81IA | 3716 | 133,621 | 9 |
| 81IA2 | 3537 | 133,367 | 11 |
| 81IB | 3495 | 132,480 | 13 |
| 81IB2 | 3567 | 134,714 | 15 |

The sequences of the deduced amino acid sequences of proteins produced by the above genes are given SEQ ID NOS. 10, 12, 14, and 16, respectively.

Endotoxin proteins have been expressed in Pseudomonas and/or Bacillus from the toxin genes. SDS-PAGE/Western blot analysis, using polyclonal antibodies directed against the "6.6 Kb" class toxin, verified that each gene encodes an immunoreactive protein of approximately 130,000 daltons. The toxin proteins encoded by the genes of the subject invention expressed in either a Bacillus or Pseudomonas host have activity against all lepidopteran insects tested: *Trichoplusia ni, Spodoptera exigua, Plutella xylostella*, and *Choristoneura occidentalis*.

The above cloning procedures were conducted using standard procedures unless otherwise noted.

The various methods employed in the preparation of the plasmids and transformation of host organisms are well known in the art. Also, methods for the use of lambda bacteriophage as a cloning vehicle, i.e., the preparation of lambda DNA, in vitro packaging, and transfection of recombinant DNA, are well known in the art. These procedures are all described in Maniatis, T., Fritsch, E. F., and Sambrook, J. (1982) Molecular Cloning: A Laboratory Manual, Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Bethesda Research Laboratories, Gaithersburg, Md. New England Biolabs, Beverly, Mass., or Boehringer-Mannheim, Indianapolis, Ind. The enzymes are used according to the instructions provided by the supplier.

The plasmids containing the B.t. toxin genes can be removed from the transformed host microbes by use of standard well-known procedures. For example, the host microbes can be subjected to cleared lysate isopycnic density gradient procedures, and the like, to recover the desired plasmid.

Example 8-Identification of Gene from PS40D1

Identification of one of the genes in PS40D1 was accomplished through amplification of an about 500 bp segment of the gene by the polymerase chain reaction (PCR). This method is now used routinely by those skilled in the art. The primers used for the amplification were primer 13 (forward) starting at base 737 of the BTSD gene (GGTATAATGTTGGATTAG) and primer 12 (reverse) starting at base 1230 (CGCAAGATTTGTATTTGC). The region sequenced from this amplified DNA extended from base 868 to base 1000.

Example 9-Characterization of B.t. Isolates and Toxin Genes by RFLP Analysis Total cellular DNA can be prepared form *Bacillus thuringiensis* (B.t.) cell grown to an optical density, at 600 nm, of 1.0. The cells can be recovered by centrifugation, and protoplasts prepared in TES buffer (30 mM Tris-Hcl, 01 mM EDTA, 50 mM NaCl, pH=8.0) containing 20 sucrose and 50 mg/ml lysozyme. The cellular material precipitated overnight at 4' C. in 100 mM (final concentration) neutral potassium chloride. The supernate can be extracted twice with phenol/chloroform (1:1). The DNA can be precipitated with ethanol and purified by isopycnic banding on a cesium chloride-ethidium brodium gradient.

Total cellular DNA isolated from B.t. cells can be digested with a restriction endonuclease and separated by electrophoresis on a 0.8% (w/v) agarose-TAE (50 mM Tris-HCl, 20 mM NaOAc, 2.5 mM EDTA, pH=8.0) buffered gel. A Southern blot gel can be hybridized with the $[^{32}P]$-radiolabeled oligonucleotide probe, ATGATTCATGCGGCAGATA, and then washed to remove unbound radioactivity. The blot can be exposed to KODAK X-OMAT ™ film using standard autoradiography techniques. The results are an array of hybridizing bands (fingerprint) which correspond to toxin gene or toxin gene fragments. This type of characterization is known as Restriction Fragment Length Polymorphism (RFLP) analysis which classifies each isolate by a distinct DNA fingerprint. Results of RFLP analysis on two B.t. isolates are shown below.

| Isolate | DNA Fingerprint Hybridizing EcoRI Fragments (Kb) |
|---|---|
| PS36A | approx. 14, 4.1 |
| PS81GG | approx. 20, 4.1, 3.3 |

Example 10-Cloning of Novel B. thuringiensis Gene Into Baculoviruses

The genes of the invention can be cloned into baculoviruses such as *Autographa Californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399–406), and pAC380, described by Smith et al. (Smith, G. E., Summers, M. D. and Fraser, M. J. [1983] Mol Cell. Biol. 3:2156-2165). The gene coding for the protein toxins to be used according to the invention can be modified with BamHI linkers at appropriate regions both upstream and downstream from the coding region and inserted into the passenger site of one of the AcNPV vectors.

Example 11-Activity Against Sheep Lice

The bioassay utilized is one whereby the sheep lice are fed on a special diet of "skin scrapings" mixed with a B.t. preparation. The diet is formulated such that 2000 μg of spray-dried B.t. preparation is mixed with each 10 mg of the skin scrapings. Mortality is monitored 24, 48, and 72 hours post inception. The results of this test are shown in Table 2.

TABLE 2

| Isolate | 72 hr Mortality |
|---|---|
| *Bacillus thuringiensis* PS40D1 | 75 |
| *Bacillus thuringiensis* PS36A | 85.5 |
| *Bacillus thuringiensis* PS86A1 | 82.5 |
| *Bacillus thuringiensis* PS71M3 | 95 |
| *Bacillus thuringiensis* PS81I | 82.5 |
| *Bacillus thuringiensis* PS81F | 98.7 |
| *Bacillus thuringiensis* PS81GG | 90 |
| *Bacillus thuringiensis* PS84C3 | 100 |

TABLE 2-continued

| Isolate | 72 hr Mortality |
|---|---|
| *Bacillus thuringiensis* PS91C2 | 75 |
| *Bacillus thuringiensis* PS92J | 91.8 |
| *Bacillus thuringiensis* PS192M4 | 75 |
| *Bacillus thuringiensis* PS192N1 | 87.8 |
| *Bacillus thuringiensis* PS201T6 | 95 |
| *Bacillus thuringiensis* PS204G6 | 80 |
| *Bacillus thuringiensis* PS211B2 | 97.5 |
| Control | 18 |

The findings disclosed above represent a novel type of activity which has utility in controlling obnoxious and economically damaging pests of livestock and humans. The above-listed B.t. can be used according to the subject invention as well as other B.t. isolates such as HD1 and related microbes. The B.t. can be used alone or in combination with a chemical pesticide for managing these insects and can be used in a variety of formulations as described above.

It should be understood that the examples and embodiments described herein are for illustrative purposes only and that various modifications or changes in light thereof will be suggested to persons skilled in the art and are to be included within the spirit and purview of this application and the scope of the appended claims.

We claim

1. A method for controlling biting lice of the order Phthiraptera, said method comprising administering to a host harboring lice, or directly onto said lice, or unto the situs of said lice, a lice controlling effective amount of a toxin from a wild-type *Bacillus thuringiensis* or a toxin encoded by a *Bacillus thuringiensis* gene which has been transformed into and expressed in a recombinant host wherein the *Bacillus thuringiensis* gene is a γ-endotoxin gene from a *Bacillus thuringiensis* strain selected from the group consisting of *Bacillus thuringiensis* PS192N1, *Bacillus thuringiensis* PS36A, *Bacillus thuringiensis* PS71M3, *Bacillus thuringiensis* PS81F, *Bacillus thuringiensis* PS92J, *Bacillus thuringiensis* PS86A1, *Bacillus thuringiensis* PS204G6, *Bacillus thuringiensis* PS81I, *Bacillus thuringiensis* PS81GG, *Bacillus thuringiensis* PS201T6, *Bacillus thuringiensis* PS84C3, *Bacillus thuringiensis* PS211B2, *Bacillus thuringiensis* PS91C2, *Bacillus thuringiensis* PS40D1 and *Bacillus thuringiensis* PS192M4.

2. The method according to claim 1, wherein said gene is selected from the group consisting of 81GG Seq ID No: 7, 81IA2 Seq ID No: 11, 81IB Seq ID No: 13, 81IB2 Seq ID No: 15, 81IA Seq ID No: 9, 40D1 Seq ID No: 3, 81F Seq ID No: 5, and 86A1 Seq ID No: 1.

3. The method, according to claim 1, wherein said host harboring said lice is sheep.

4. The method, according to claim 1, wherein said biting lice is of the suborder Mallophaga or Anoplura.

5. The method, according to claim 1, wherein said biting lice is of the genus Damilinia.

6. The method, according to claim 1, wherein said lice is *Damilinia ovis*.

7. The method, according to claim 1, which further comprises administration of one or more additional lice-controlling compounds.

8. The method, according to claim 1, wherein said toxin is administered as a drench.

9. A composition for the control of lice wherein said composition comprises an isolated wild-type *Bacillus thuringiensis*, or a toxin encoded by a *Bacillus thuringiensis* gene which has been transformed into and expressed in a recombinant host; said composition further comprising a carrier suitable for application of a lice-controlling agent wherein the *Bacillus thuringiensis* gene is a γ-endotoxin gene from a *Bacillus thuringiensis* strain selected from the group consisting of *Bacillus thuringiensis* PS192N1, *Bacillus thuringiensis* PS36A, *Bacillus thuringiensis* PS71M3, *Bacillus thuringiensis* PS81F, *Bacillus thuringiensis* PS92J, *Bacillus thuringiensis* PS86A1, *Bacillus thuringiensis* PS204G6, *Bacillus thuringiensis* PS81I, *Bacillus thuringiensis* PS81GG, *Bacillus thuringiensis* PS201T6, *Bacillus thuringiensis* PS84C3, *Bacillus thuringiensis* PS211B2, *Bacillus thuringiensis* PS91C2, *Bacillus thuringiensis* PS40D1 and *Bacillus thuringiensis* PS192M4.

10. The composition, according to claim 9, which further comprises one or more additional lice-controlling compounds.

11. A biologically pure culture selected from the group consisting of *Bacillus thuringiensis* PS36A, *Bacillus thuringiensis* PS91C2, and *Bacillus thuringiensis* PS192M4.

12. The biologically pure culture, according to claim 11, *Bacillus thuringiensis* PS36A, having the identifying characteristics of NRRL B-18929.

13. The biologically pure culture, according to claim 11, *Bacillus thuringiensis* PS91C2, having the identifying characteristics of NRRL B-18931.

14. The biologically pure culture, according to claim 11, *Bacillus thuringiensis* PS192M4, having the identifying characteristics of NRRL B-18932.

* * * * *

UNITED STATES PATENT AND TRADEMARK OFFICE
CERTIFICATE OF CORRECTION

PATENT NO.    :    5,273,746

DATED         :    December 28, 1993

INVENTOR(S)   :    Jewel Payne and Leslie A. Hickle

It is certified that error appears in the above-identified patent and that said Letters Patent is hereby corrected as shown below:

Column 2     line 61: After "utilized as" insert --a--.

Column 4     line 26: Delete "PS811" and insert --PS81I--.

Column 11    line 50: After "will vary" insert --widely--.

Column 12    line 50: Delete "31:39" and insert --21:39--.

Column 21    line 2: After "are given" insert --in--.

Column 22    line 67: Delete "98.7" and insert --89.7--.

Signed and Sealed this

Second Day of August, 1994

Attest:

BRUCE LEHMAN

*Attesting Officer*          *Commissioner of Patents and Trademarks*